(12) United States Patent
Yamane et al.

(10) Patent No.: US 12,260,961 B2
(45) Date of Patent: Mar. 25, 2025

(54) GENERATION DEVICE AND GENERATION METHOD

(71) Applicant: SONY GROUP CORPORATION, Tokyo (JP)

(72) Inventors: Kenji Yamane, Tokyo (JP); Shinji Watanabe, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 381 days.

(21) Appl. No.: 17/774,919

(22) PCT Filed: Nov. 9, 2020

(86) PCT No.: PCT/JP2020/041783
§ 371 (c)(1),
(2) Date: May 6, 2022

(87) PCT Pub. No.: WO2021/095698
PCT Pub. Date: May 20, 2021

(65) Prior Publication Data
US 2022/0399118 A1    Dec. 15, 2022

(30) Foreign Application Priority Data
Nov. 15, 2019 (JP) .................. 2019-206862

(51) Int. Cl.
*G16H 50/20* (2018.01)
*G06T 7/00* (2017.01)
*G16H 30/40* (2018.01)

(52) U.S. Cl.
CPC ........... *G16H 50/20* (2018.01); *G06T 7/0014* (2013.01); *G16H 30/40* (2018.01); *G06T 2207/10056* (2013.01); *G06T 2207/20081* (2013.01)

(58) Field of Classification Search
CPC ...... G16H 50/20; G16H 30/40; G06T 7/0014; G06T 2207/10056; G06T 2207/20081;
(Continued)

(56) References Cited

U.S. PATENT DOCUMENTS 8,787,642 B2    7/2014 Li
11,080,855 B1 *  8/2021 Beck ................ G16H 50/30
(Continued)

FOREIGN PATENT DOCUMENTS

CN    109872814    *   6/2019
CN    110197714 A      9/2019
(Continued)

OTHER PUBLICATIONS

International Search Report and Written Opinion of PCT Application No. PCT/JP2020/041783, issued on Dec. 8, 2020, 09 pages of ISRWO.

*Primary Examiner* — Jerome Grant, II
(74) *Attorney, Agent, or Firm* — CHIP LAW GROUP

(57) ABSTRACT

The generation device 100 according to the present application includes an acquisition unit 131 and a generation unit 134. The acquisition unit 131 acquires a first pathological image captured and an annotation that is information added to the first pathological image and is meta information related to the first pathological image. The generation unit 134 generates learning data for evaluating pathological-related information based on a second pathological image according to the second pathological image different from the first pathological image, the learning data being learning data obtained by transcribing the annotation in a manner corresponding to the second pathological image.

13 Claims, 17 Drawing Sheets

(58) Field of Classification Search
CPC ......... G06T 7/0012; G06T 2207/20084; G06T 2207/30204; G06N 20/00
USPC ........................................................ 382/131
See application file for complete search history.

(56) References Cited

U.S. PATENT DOCUMENTS

| | | | |
|---|---|---|---|
| 2017/0322124 A1* | 11/2017 | Barnes .................. | G06T 7/0014 |
| 2018/0308565 A1* | 10/2018 | Pinter .................... | G06N 20/00 |
| 2019/0006027 A1* | 1/2019 | Sacaleanu .............. | G16H 50/30 |
| 2019/0266486 A1 | 8/2019 | Yamada et al. | |
| 2020/0294654 A1* | 9/2020 | Harzig ................... | G16H 15/00 |
| 2021/0327059 A1* | 10/2021 | Lee ....................... | G06T 7/0014 |

FOREIGN PATENT DOCUMENTS

| | | | |
|---|---|---|---|
| CN | 108510482 | * | 12/2020 |
| EP | 3531339 A1 | | 8/2019 |
| JP | 2011-133849 A | | 7/2011 |
| JP | 2019-109577 A | | 7/2019 |
| JP | 2019-148950 A | | 9/2019 |

* cited by examiner

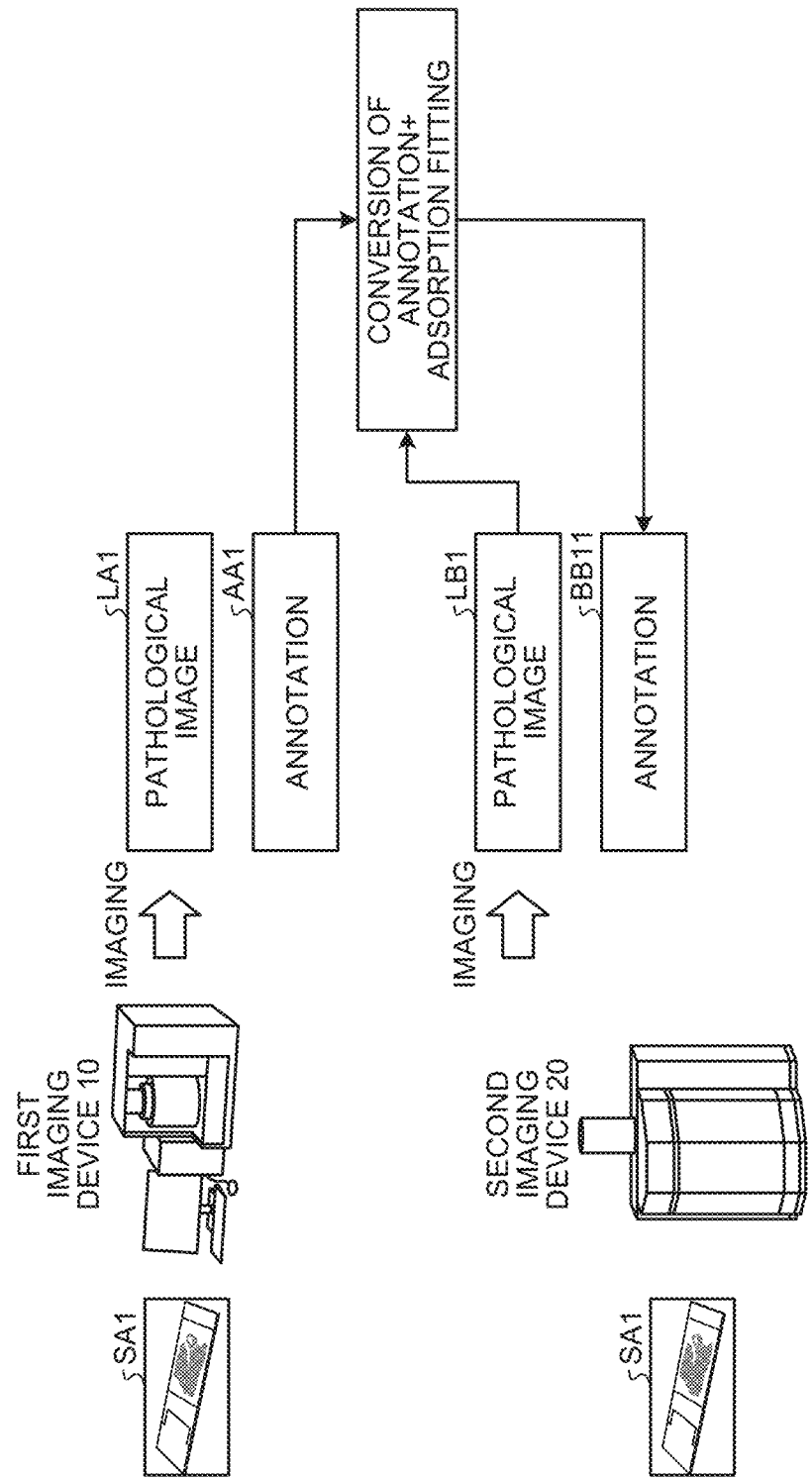

FIG.7

| SLIDE ID | SLIDE DATA STORAGE PATH | ... |
|---|---|---|
| DS1 | /data/hoge1 | ... |
| DS2 | /data/hoge2 | ... |
| ... | ... | ... |

FIG.8

| SLIDE ID | SLIDE DATA | ... |
|---|---|---|
| DS1 | SLIDE DATA #1 | ... |
| DS2 | SLIDE DATA #2 | ... |
| ... | ... | ... |

| ANNOTATION ID | SLIDE ID | ANNOTATION DATA | LABEL | ... |
|---|---|---|---|---|
| DA1 | DS1 | A1_1.xml | CANCER | ... |
| DA2 | DS1 | A2_1.xml | NON-CANCER | ... |
| DA3 | DS1 | A3_1.xml | CANCER | ... |
| DA4 | DS2 | A4_2.xml | NON-CANCER | ... |
| ... | ... | ... | ... | ... |

FIG.11

| NEW SLIDE ID | NEW SLIDE DATA STORAGE PATH | ... |
|---|---|---|
| DS11 | /data/hoge11 | ... |
| DS22 | /data/hoge22 | ... |
| ... | ... | ... |

FIG.12

| NEW SLIDE ID | NEW SLIDE DATA | ... |
|---|---|---|
| DS11 | SLIDE DATA #11 | ... |
| DS22 | SLIDE DATA #22 | ... |
| ... | ... | ... |

FIG.13

| TRANSCRIPTION ANNOTATION ID | NEW SLIDE ID | TRANSCRIPTION ANNOTATION DATA | LABEL | ... |
|---|---|---|---|---|
| DA11 | DS11 | A11_1.xml | CANCER | ... |
| DA22 | DS22 | A22_1.xml | NON-CANCER | ... |
| DA33 | DS33 | A33_1.xml | CANCER | ... |
| ... | ... | ... | ... | ... |

| CORRECTION ANNOTATION ID | NEW SLIDE DATA | TRANSCRIPTION ANNOTATION DATA | LABEL | ... |
|---|---|---|---|---|
| DA111 | SLIDE DATA #11 | A11_1.xml | CANCER | ... |
| DA222 | SLIDE DATA #22 | A22_1.xml | NON-CANCER | ... |
| DA333 | SLIDE DATA #33 | A33_1.xml | CANCER | ... |
| ... | ... | ... | ... | ... |

| MODEL ID | MODEL (CALCULATION FORMULA) |
|---|---|
| DM11 | MODEL #11 |
| DM22 | MODEL #22 |
| ... | ... |

FIG.16

| COORDINATE CONVERSION ID | COORDINATE CONVERSION INFORMATION | ... |
|---|---|---|
| DX11 | COORDINATE CONVERSION #11 | ... |
| DX22 | COORDINATE CONVERSION #22 | ... |
| DX33 | COORDINATE CONVERSION #33 | ... |
| ... | ... | ... |

| VALUE | VALUE IN PREVIOUSLY CAPTURED IMAGE | VALUE IN NEWLY CAPTURED IMAGE |
|---|---|---|
| VERTICAL um/pix | 5 | 2 |
| HORIZONTAL um/pix | 10 | 5 |

GENERATION DEVICE AND GENERATION METHOD

FIELD

The present invention relates to a generation device and a generation method.

BACKGROUND

In the medical or pathological field or the like, an image of a section of a cell, a tissue, an organ, or the like of a living body obtained by an optical microscope may be digitized. Then, a doctor, a pathologist, or the like may diagnose a patient on the basis of the digital image that is a digitized image.

As one advantage of the digitization of the pathological image, information can be added to a predetermined region of the image. Here, the information added to the predetermined region of the image is a remark attached to a region where a lesion may exist or the like as a region to which a pathologist or the like needs to pay attention (hereinafter referred to appropriately as "annotation"). As another advantage, a learning model for properly estimating information such as a case or a disease name is generated by learning the information added to the predetermined region of the image. Here, the learning model is, for example, a model for estimating a binary classification such as cancer or non-cancer. As another example, the learning model is a model for estimating a detailed classification such as a progression stage of cancer.

Conventionally, it has been known that an annotation is added to a pathological image to facilitate visual observation, thereby assisting a pathologist in diagnosis (see Patent Literature 1).

CITATION LIST

Patent Literature

Patent Literature 1: JP 2011-133849 A

SUMMARY

Technical Problem

In the conventional art, in a case where an imaging device used when learning data used to generate a learning model is captured (hereinafter referred to appropriately as "imaging device for learning") is different from an imaging device used when a target to be evaluated is imaged (hereinafter referred to appropriately as "imaging device for evaluation"), even though the learning model is generated using the imaging device for learning, since there is a difference between the imaging devices, there is a possibility that the learning model generated using the imaging device for learning may fail to properly evaluate information captured by the imaging device for evaluation.

The present application has been made in view of the above, and an object thereof is to promote assistance in diagnosing an identification target.

Solution to Problem

A generation device according to the present disclosure includes: an acquisition unit that acquires a first pathological image captured, and an annotation that is information added to the first pathological image and is meta information related to the first pathological image; and a generation unit that generates learning data for evaluating pathological-related information based on a second pathological image according to the second pathological image different from the first pathological image, the learning data being learning data obtained by transcribing the annotation in a manner corresponding to the second pathological image.

BRIEF DESCRIPTION OF DRAWINGS

FIG. 3 is a diagram illustrating an example of information processing according to the embodiment.

FIG. 7 is a diagram illustrating an example of a slide storage unit according to the embodiment.

FIG. 8 is a diagram illustrating an example of a slide data storage unit according to the embodiment.

FIG. 11 is a diagram illustrating an example of a new slide storage unit according to the embodiment.

FIG. 12 is a diagram illustrating an example of a new slide data storage unit according to the embodiment.

FIG. 13 is a diagram illustrating an example of a transcription annotation storage unit according to the embodiment.

FIG. 14 is a diagram illustrating an example of a correction annotation storage unit according to the embodiment.

FIG. 15 is a diagram illustrating an example of a model storage unit according to the embodiment.

FIG. 16 is a diagram illustrating an example of a coordinate conversion information storage unit according to the embodiment.

DESCRIPTION OF EMBODIMENTS

Hereinafter, modes for carrying out a generation device and a generation method according to the present application (hereinafter referred to as "embodiments") will be described in detail with reference to the drawings. Note that the generation device and the generation method according to the present application are not limited by these embodiments. In addition, in the following embodiments, the same parts are denoted by the same reference signs, and redundant description will be omitted.

The present disclosure will be described according to the following order of items.
1. Configuration of Information Processing System
2. Example of Information Processing When Imaging Device for Learning and Imaging Device for Evaluation are Same
3. Example of Information Processing When Imaging Device for Learning and Imaging Device for Evaluation are Different
4. Configuration of Generation Device
5. Flow of Information Processing
6. Variation on Processing
6-1. Type of Label
6-2. Provision of Estimation Result
6-3. Learning Method
6-4. Pathological Subject
6-5. Imaging Subject
6-6. Annotation Conversion Method Using Coordinate Information
6-7. Annotation Conversion Method Using Format of Imaging Device
6-8. Annotation According to Embodiment
6-9. Slide According to Embodiment
6-10. Conversion of Annotation
6-11. Learning Data
6-12. Identification of Slide Using Pathological Case Number
7. Hardware Configuration
8. Others

EMBODIMENTS

[1. Configuration of Information Processing System]

Figure 1:
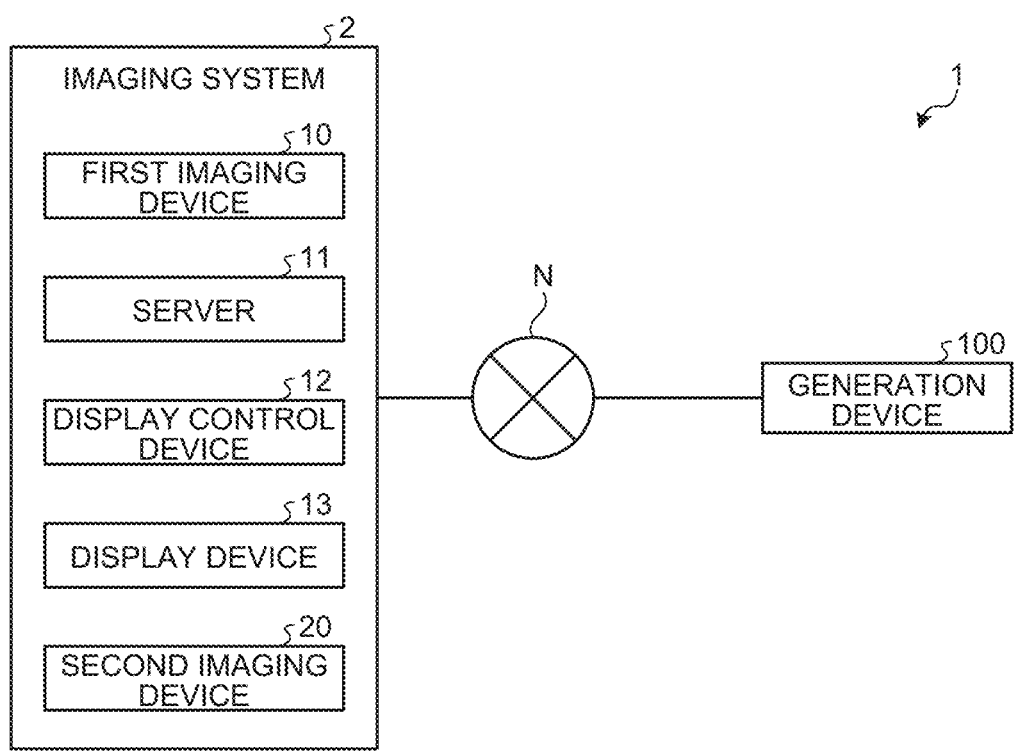
FIG. 1 is a diagram illustrating a configuration example of an information processing system according to an embodiment.

A configuration of an information processing system 1 will be described with reference to FIG. 1. FIG. 1 is a diagram illustrating a configuration example of an information processing system according to an embodiment. As illustrated in FIG. 1, the information processing system 1 includes an imaging system 2 and a generation device 100. The imaging system 2 and the generation device 100 are communicably connected to each other in a wired or wireless manner via a predetermined communication network (network N). FIG. 1 is a diagram illustrating a configuration example of an information processing system according to an embodiment. Note that the information processing system 1 illustrated in FIG. 1 may include a plurality of imaging systems 2 and a plurality of generation devices 100.

The imaging system 2 is a system mainly used by a pathologist (hereinafter referred to as "user"), and is applied to, for example, a laboratory or a hospital. As illustrated in FIG. 1, the imaging system 2 includes a first imaging device 10, a server 11, a display control device 12, and a display device 13.

The first imaging device 10 is an imaging device that images an observation subject placed on a slide and generates a pathological image (an example of a medical image) (hereinafter referred to appropriately as "first pathological image") that is a digital image. The observation subject is, for example, a tissue or a cell collected from a patient, such as a piece of flesh of an organ, saliva, or blood. An annotation based on the annotation added to the first pathological image by a pathologist or the like is learning data according to the embodiment. Specifically, an annotation added to the first pathological image by the pathologist or the like, a transcription annotation and a correction annotation to be described later, and the like are learning data according to the embodiment. For example, the first imaging device 10 generates learning data for estimating a binary classification such as cancer or non-cancer. The first imaging device 10 transmits the captured first pathological image to the generation device 100 or the like via the network N. For example, the first imaging device 10 transmits the captured first pathological image and annotation information that is information regarding the annotation added to the first pathological image to the generation device 100. Here, the annotation information includes position information indicating a position of the annotation and additional information that is information added to the annotation. The position information for the annotation is coordinate information for the annotation added to the pathological image by the user. Note that the annotation information may include image information for the annotation instead of the position information for the annotation such as the coordinate information. The additional information for the annotation is, for example, remark information indicating a remark about the annotation. For example, the remark information for the annotation is information regarding a medical condition, a disease site, or the like. Specifically, the information indicating the remark about the annotation is a label indicating a medical condition of the patient, such as "cancer" or "non-cancer".

The server 11 is a device that stores and holds the first pathological image captured by the first imaging device 10 in a storage unit, which is not illustrated. When receiving a browsing request from the display control device 12, the server 11 searches the storage unit, which is not illustrated, for the first pathological image and transmits the retrieved first pathological image to the display control device 12.

Furthermore, the server 11 is a device that stores and holds an annotation added by the user to the first pathological image displayed on the display device 13 in the storage unit, which is not illustrated.

Information regarding diagnosis by the user is accumulated in the server 11 every day. That is, the first pathological image captured by the first imaging device 10 and the annotation added to the first pathological image are stored in the server 11.

The display control device 12 transmits the browsing request for the first pathological image received from the user to the server 11. Then, the display control device 12 controls the display device 13 to display the first pathological image received from the server 11.

The display device 13 includes a screen using, for example, liquid crystal, electro-luminescence (EL), cathode ray tube (CRT), or the like. The display device 13 may be compatible with 4K or 8K, or may be formed by a plurality of display devices. The display device 13 displays the first pathological image that the display device 13 is controlled to display by the display control device 12.

In addition, the display device 13 receives a user's operation on the displayed first pathological image. When receiving an annotation added by the user, the display device 13 transmits the annotation to the server 11. Furthermore, the display device 13 may transmit the first pathological image to which the annotation has been added to the server 11.

A second imaging device 20 is an imaging device replaced from the first imaging device 10 and is a newer imaging device than the first imaging device 10. The second imaging device 20 transmits a second pathological image to the generation device 100 or the like via the network N.

The generation device 100 is an information processing device, e.g., a PC or a work station (WS), and performs processing on the basis of information transmitted from the first imaging device 10, the second imaging device 20, and the like via the network N. In addition, the generation device 100 transcribes the annotation added to the first pathological image to the second pathological image on the basis of the first pathological image and the second pathological image. Then, the generation device 100 corrects the annotation transcribed to the second pathological image on the basis of adsorption fitting processing, which will be described later. In this way, the generation device 100 generates learning data that is data used for estimating pathological information such as a case and a disease name.

The information processing system 1 has been briefly described so far. Hereinafter, a configuration of the generation device 100 and its processing will be described in detail, but various types of information (pathological image, annotation, learning model, etc.) that are required for the description will be first described.

[2. Example of Information Processing when Imaging Device for Learning and Imaging Device for Evaluation are Same]

Figure 2:
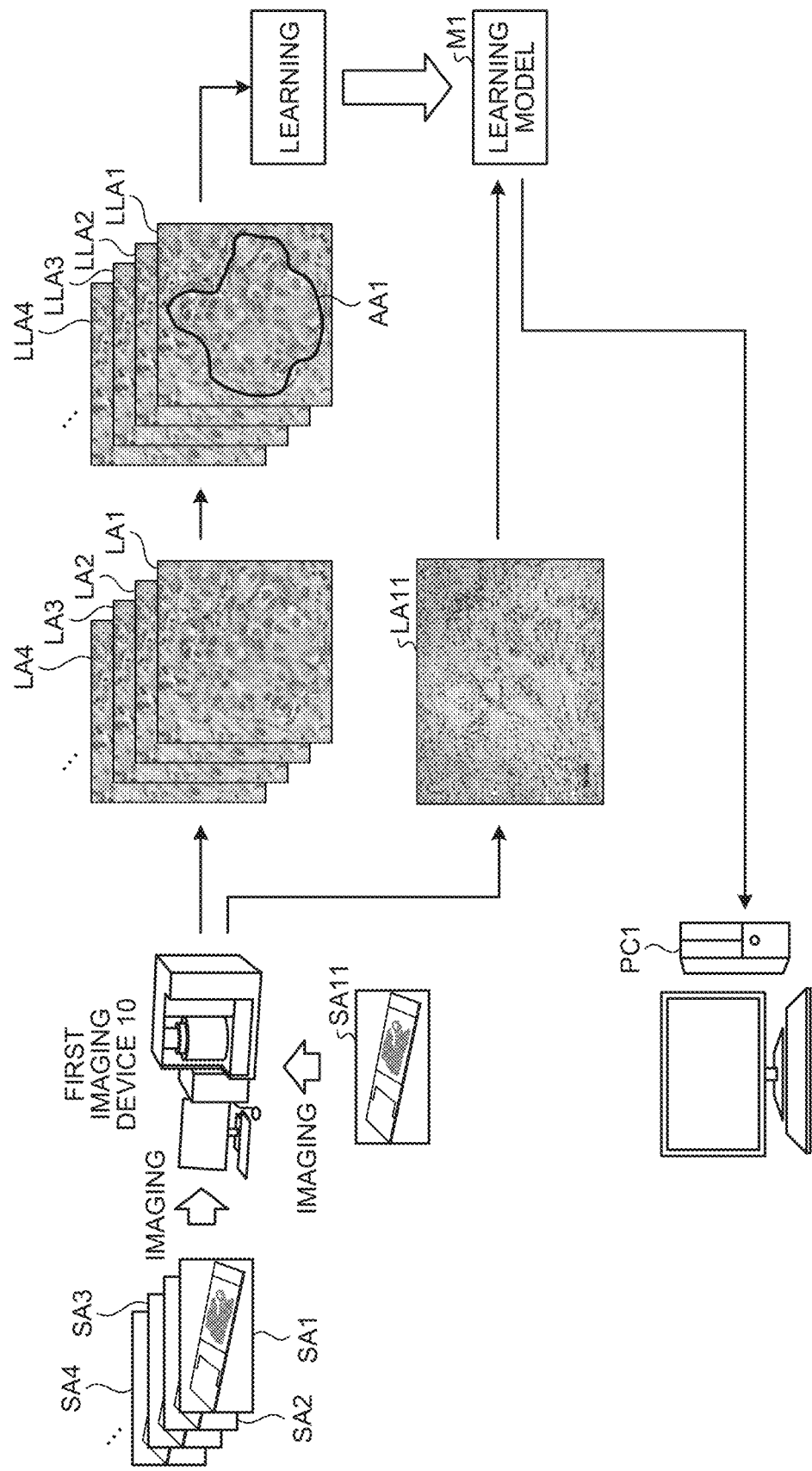
FIG. 2 is a diagram illustrating an example of information processing according to the embodiment.

FIG. 2 illustrates a case where a learning model is generated on the basis of the first pathological images captured by the first imaging device 10 and the annotation information added to the first pathological images. Hereinafter, the learning model generated on the basis of the annotations added to the first pathological images will appropriately be referred to as "learning model M1". Furthermore, FIG. 2 illustrates a case where a first pathological image newly captured by the first imaging device 10 is diagnosed.

Hereinafter, an example of information processing according to the embodiment will be described with reference to FIG. 2.

Slides SA1 to SA4 are slides imaged by the first imaging device 10. Further, a slide SA11 is a slide imaged by the first imaging device 10. Note that the slide may hereinafter be mentioned as pathological subject. In addition, the number of slides required for generating the learning model M1 according to the embodiment is not limited. Although FIG. 2 illustrates a case where the first imaging device 10 images a total of four slides SA1 to SA4, the number of slides imaged by the first imaging device 10 may be three or less or five or more.

Pathological images LA1 to LA4 are pathological images obtained by imaging the slides SA1 to SA4. In addition, a pathological image LA11 is a pathological image of the slide SA11. Note that the numerals in the reference signs for the slides correspond to those for the pathological images, respectively. For example, the pathological image LA1 is image information for the slide SA1.

Pathological images LLA1 to LLA4 are pathological images obtained by adding annotations to the pathological images LA1 to LA4. Hereinafter, the numerals in the reference signs for the slides correspond to those for the pathological images to which the annotations are added, respectively. In addition, the numerals in the reference signs for the slides correspond to those for the annotations, respectively. For example, the annotations corresponding to the pathological images LLA1 to LLA4 are annotations AA1 to AA4. Note that, although not illustrated in FIG. 2, remark information for the annotations may be added to the pathological images LLA1 to LLA4. For example, as the remark information for the annotations, labels may be added to the pathological images LLA1 to LLA4. For example, labels such as "label 1A" and "label 1B" may be added to the pathological images LLA1 to LLA4.

The learning model M1 is a model generated by learning the annotation information for the pathological images LLA1 to LLA4. For example, the learning model M1 is a model generated by learning the additional information for the annotation. As a specific example of processing, the learning model M1 is a model generated by learning an annotation to which label "cancer" is added as correct answer information when the label of the annotation is "cancer". In addition, as a pathological image is input, the learning model M1 outputs a probability that a lesion is included in the pathological image. For example, as a pathological image is input, the learning model M1 outputs a probability that a region indicating a lesion is included in the pathological image.

Since the learning model M1 is generated on the basis of the first pathological images captured by the first imaging device 10, a first pathological image captured by the first imaging device 10 can be appropriately evaluated using the learning model M1.

It has been described above that the evaluation processing is performed by inputting a new pathological image captured by the first imaging device 10 to the learning model M1 generated on the basis of the pathological images captured by the first imaging device 10.

However, if a new pathological image captured by the second imaging device 20 different from the first imaging device 10 is evaluated using the learning model generated on the basis of the pathological images captured by the first imaging device 10, since the pathological images are different in color, magnification, resolution, etc. between the imaging devices, it is not always possible that the above-described learning model outputs appropriate information. Therefore, in the information processing described above, there is a possibility that a pathological image captured by another imaging device such as the second imaging device 20 cannot be appropriately evaluated.

This will be described in detail. For example, in a case where the first imaging device 10 is replaced with the second imaging device 20, since the second imaging device 20 is a newer imaging device than the first imaging device 10, the second imaging device 20 may have a higher resolution. In this case, if a second pathological image captured by the second imaging device 20 having a high resolution is evaluated using the learning model generated using the first pathological images captured by the first imaging device 10 having a low resolution, there is a possibility that the evaluation cannot be appropriately performed because of the different resolution.

As another problem caused by the replacement from the first imaging device 10 to the second imaging device 20, there may be no pathological image captured by the second imaging device 20, while there are first pathological images captured by the first imaging device 10. For example, in a case where the user just replaces the first imaging device 10 with the second imaging device 20, there may be only the pathological images captured by the first imaging device 10 and the learning model M1 using the pathological images captured by the first imaging device 10. If the slides for the pathological images captured by the first imaging device 10 are stored, the slides can be captured again using the second imaging device 20. However, it may be difficult for the user to accurately add annotations to the pathological images captured again using the second imaging device 20. In addition, a lot of time and many operators are required to add these annotations. In a case where the annotations cannot be accurately added, it is difficult to generate a learning model for appropriately estimating pathological information using the pathological images obtained by imaging the slides using the second imaging device 20.

In order to generate a learning model capable of appropriate diagnosis, the following method is used in the present embodiment. Specifically, the generation device 100 transcribes annotations to the pathological images captured by the second imaging device 20 on the basis of the annotations added to the pathological images captured by the first imaging device 10. By transcribing the annotations to the pathological images captured again by the second imaging device 20 on the basis of the pathological images captured by the first imaging device 10 as described above, the generation device 100 can easily generate a learning model (hereinafter referred to appropriately as "learning model M2") based on the pathological images captured by the second imaging device 20. By using the learning model M2, the generation device 100 can estimate pathological information with high accuracy even from a pathological image newly captured by the second imaging device 20.

Hereinafter, information processing for diagnosing a second pathological image captured by the second imaging device 20 will be described with reference to FIG. 3. Note that the same description as that for FIG. 2 will be appropriately omitted.

[3. Example of Information Processing When Imaging Device for Learning and Imaging Device for Evaluation are Different]

FIG. 3 illustrates a case where the annotations added to the first pathological images are transcribed to the second pathological images captured by the second imaging device 20. Note that, in FIG. 3, the same slide as imaged by the first imaging device 10 is imaged by the second imaging device 20 as well. Furthermore, according to the embodiment, the annotation is converted on the basis of the coordinate information for the first pathological image and the coordinate information for the second pathological image. Then, in the embodiment, the annotation of the first pathological image is transcribed to corresponding coordinates of the second pathological image.

Hereinafter, processing by the generation device 100 for generating learning data in which the annotation is transcribed to correspond to the second pathological image will be described. Note that, an annotation after the transcription of the annotation will hereinafter be referred to appropriately as "transcription annotation". In addition, hereinafter, an annotation after adsorption fitting processing, which is processing of fitting the transcription annotation along a boundary of a feature on the pathological image, will be appropriately referred to as "correction annotation". Although the transcription annotation and the correction annotation are distinguished from each other in the embodiment, they may be the same annotation. For example, when the adsorption fitting processing is not performed, the transcription annotation and the correction annotation may be the same annotation.

A slide SA1 is a slide previously imaged by the first imaging device 10. A pathological image LA1 is an image generated when the slide SA1 was previously imaged. In addition, an annotation has already been added to the pathological image LA1 by a pathologist or the like. Further, the slide SA1 is imaged again by the second imaging device 20 as well. A pathological image LB1 is an image generated by imaging the slide SA1, which has been imaged by the first imaging device 10, again using the first imaging device 10. In FIG. 3, on the basis of the pathological image LA1 and the annotation AA1, an annotation BB1 is generated by converting the annotation to correspond to the pathological image LB1. Then, an annotation BB11 is generated by performing adsorption fitting on the annotation BB1. Hereinafter, generation processing according to the embodiment will be described with reference to FIGS. 4 and 5.

Figures 4A, 4B:
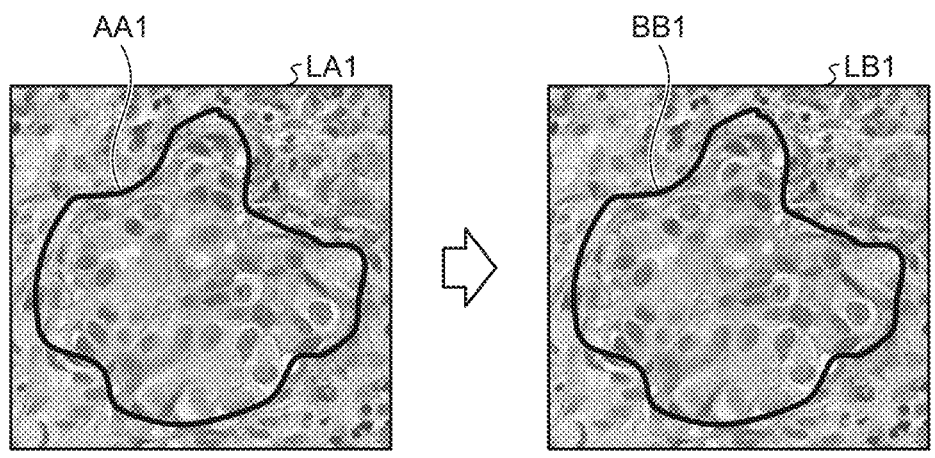
FIG. 4 is a diagram illustrating an example of information processing according to the embodiment.

FIG. 4(a) illustrates the pathological image LA1. In FIG. 4(a), the annotation AA1 is added to the medical image LA1.

FIG. 4(b) illustrates the pathological image LB1. In FIG. 4(b), the annotation BB1 is added to the pathological image LB1. The annotation BB1 is an annotation generated by converting the annotation AA1 to correspond to the pathological image LB1.

Figure 5C:
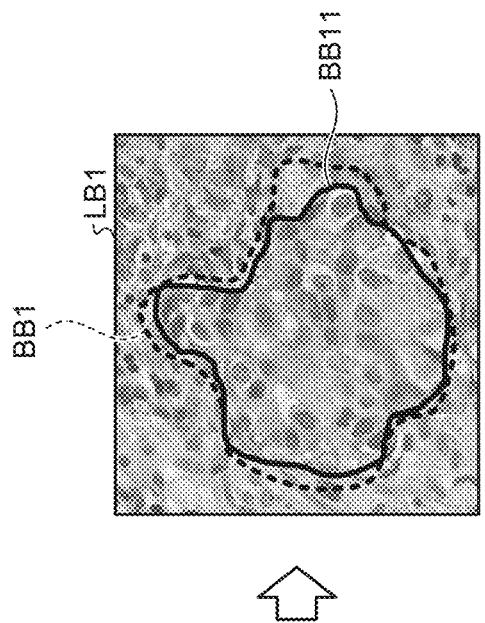
FIG. 5 is a diagram illustrating an example of information processing according to the embodiment.
Figure 5B:
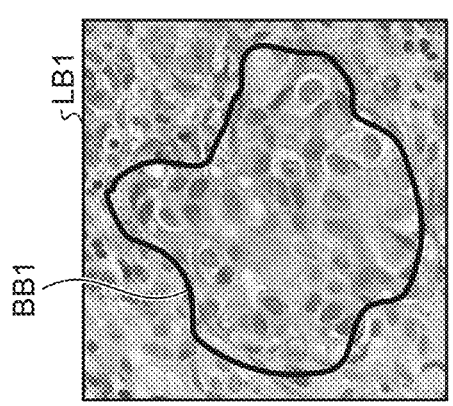
Figure 5A:
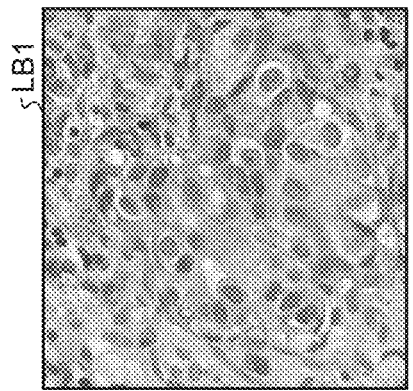

FIG. 5(a) illustrates the pathological image LB1.

FIG. 5(b) illustrates the pathological image LB1 to which the annotation BB1 is added. As illustrated in FIG. 5(b), the generation device 100 transcribes the annotation BB1 based on the annotation AA1 of the pathological image LA1 to the pathological image LB1. For example, the generation device 100 transcribes the annotation BB1 obtained by converting the annotation AA1, which is an annotation of a slide recognized to be the same as that for the pathological image LB1. Note that, if the slide can be uniquely identified on the basis of the label information, the same slide as that imaged by the second imaging device 20 can be efficiently and effectively specified.

As illustrated in FIG. 5(b), the generation device 100 transcribes the annotation BB1 subjected to conversion to correspond to the pathological image LB1. For example, the generation device 100 converts the annotation AA1, which is a base annotation, into the annotation BB1 corresponding to the pathological image LB1 based on the coordinate information for the pathological image LA1 and the pathological image LB1. Here, the annotation BB1 is a transcription annotation according to the embodiment. Hereinafter, conversion processing according to the embodiment will be described.

As described above, the annotation added by the first imaging device 10 is converted to correspond to the second imaging device 20. For example, the annotation added in the first imaging device 10 is converted into that in a format of the second imaging device 20 on the basis of the coordinate information for the first pathological image captured by the first imaging device 10 and the coordinate information for the second pathological image captured by the second imaging device 20. As a specific example, the coordinate information for the annotation added in the first imaging device 10 is converted into that in the format of the second imaging device 20 by comparing the coordinate information for the pathological image captured by the second imaging device 20 with the coordinate information for the pathological image captured by the first imaging device 10. For example, the annotation added in the first imaging device 10 is converted into that based on coordinate information corresponding to the format of the second imaging device 20 using predetermined coordinate conversion information (e.g., coordinate conversion table). For example, the annotation added in the first imaging device 10 is converted into that based on coordinate information corresponding to the format of the second imaging device 20 using coordinate conversion data stored in the predetermined storage unit.

In FIG. 5(*c*), a correction annotation BB11, which is an annotation for learning, is generated from the transcription annotation BB1 and the pathological image LB1. For example, the correction annotation is generated by adsorption-fitting the transcription annotation on the basis of the second pathological image. The adsorption fitting may be performed using a graph cut technique or the like. Accordingly, an accurate and uniform annotation can be generated.

By using the correction annotation as described above, the generation device 100 has the following effects. For example, even in a case where the first imaging device 10 and the second imaging device 20 are different in resolution or pathological images are different in quality according to the difference in imaging condition, the generation device 100 can add a more appropriate annotation by performing the adsorption fitting processing. As a result, the generation device 100 can generate a higher-quality learning model.

In this case, the generation device 100 assists pathological diagnosis by using a learning model M2 newly trained by learning the correction annotations converted to correspond to the pathological images LB1. In addition, the newly trained learning model M2 according to the embodiment is a learning model newly generated on the basis of the second pathological images in order to diagnose a second pathological image on the basis of the information captured by the first imaging device 10. For example, the newly trained learning model M2 according to the embodiment is a learning model newly trained on the basis of the second pathological images and the annotations corrected based on the first pathological images and the second pathological images.

The generation device 100 provides a learning model M2 generated by learning the correction annotations. For example, the generation device 100 provides a learning model M2 that estimates a second pathological image when the second pathological images captured by the second imaging device 20 are input.

The generation device 100 acquires a result of diagnosis by a pathologist or the like with respect to the estimation result and labels the correction annotation. For example, the generation device 100 transmits the learning model M2 to the imaging system 2, acquires a result of diagnosis by a pathologist or the like with respect to the result of estimation using the transmitted learning model M2, and labels the correction annotation For example, in a case where the estimation result is cancer and the result of diagnosis by the pathologist or the like with respect to the estimation result is also cancer, the generation device 100 adds a label such as "cancer" to the correction annotation. In this way, the generation device 100 generates correct answer information for the learning model M2.

As described above, the information processing according to the embodiment includes the following processing.

(1) A slide imaged by the first imaging device 10 is imaged by the second imaging device 20.
(2) The slide imaged by the second imaging device 20 and imaged by the first imaging device 10 is identified using image processing.
(3) An annotation added in the first imaging device 10 is converted into that in the format of the second imaging device 20.
(4) The annotation is converted into a correction annotation using image processing based on the pathological image captured by the second imaging device 20 and the converted annotation.
(5) After the conversion into the correction annotation, the correction annotation is learned based on labels of previous slides as teacher data.

Accordingly, the imaging device can be changed over in a simple manner.

The various types of information processing illustrated in FIGS. 2 to 5 are not limited to what has been described above, and may be performed in various forms. This will be described below.

[4. Configuration of Generation Device]

Figure 6:
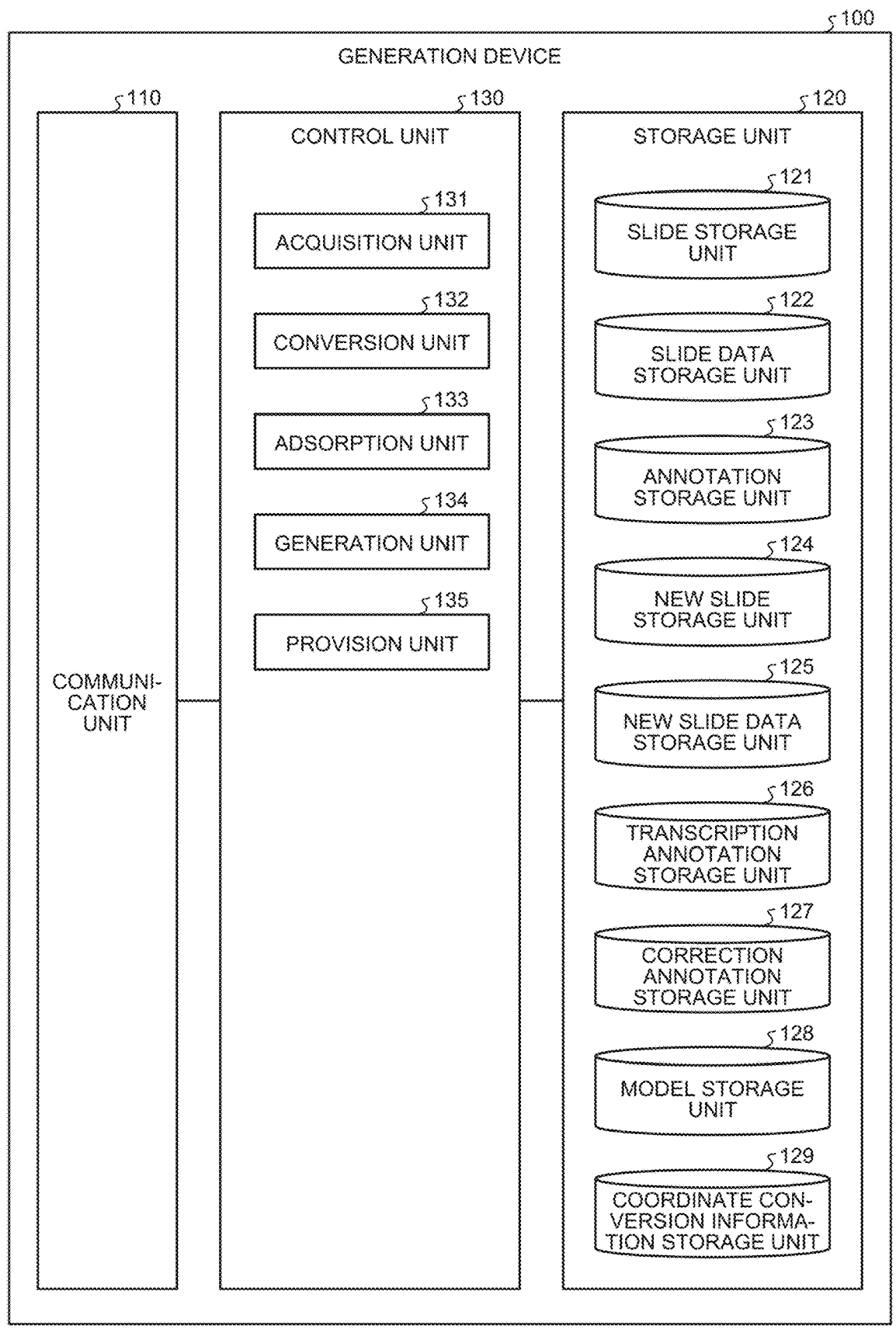
FIG. 6 is a diagram illustrating a configuration example of a generation device according to the embodiment.

Next, a configuration of the generation device 100 according to the embodiment will be described with reference to FIG. 6. FIG. 6 is a diagram illustrating a configuration example of the generation device 100 according to the embodiment. As illustrated in FIG. 6, the generation device 100 includes a communication unit 110, a storage unit 120, and a control unit 130. The generation device 100 may include an input unit (e.g., a keyboard or a mouse) for receiving various operations from an administrator of the generation device 100, and a display unit (e.g., a liquid crystal display) for displaying various types of information.

(Communication Unit 110)

The communication unit 110 is realized by, for example, an NIC or the like. The communication unit 110 is connected to a network N in a wired or wireless manner to transmit and receive information to and from the first imaging device 10 and the like via the network N.

(Storage Unit 120)

The storage unit 120 is realized by, for example, a semiconductor memory element such as a RAM or a flash memory, or a storage device such as a hard disk or an optical disk. As illustrated in FIG. 6, the storage unit 120 includes a slide storage unit 121, a slide data storage unit 122, an annotation storage unit 123, a new slide storage unit 124, a new slide data storage unit 125, a transcription annotation storage unit 126, a correction annotation storage unit 127, a model storage unit 128, and a coordinate conversion information storage unit 129.

The slide storage unit 121 stores information regarding slides imaged by the first imaging device 10. The slide storage unit 121 stores information regarding slide data storage paths. Here, FIG. 7 illustrates an example of the slide storage unit 121 according to the embodiment. As illustrated in FIG. 7, the slide storage unit 121 includes items such as "slide ID" and "slide data storage path".

The "slide ID" indicates identification information for identifying a slide. The "slide data storage path" indicates information regarding a storage destination in which slide data is stored. For example, the "slide data storage path" indicates path information for the storage destination. For example, the "slide data storage path" indicates a path stored in the slide data storage unit 122. For example, the "slide data storage path" may be a URL where the slide data is located, a file path name of the storage destination, or the like. In the example of FIG. 7, it is illustrated that the slide data storage path of the slide identified as the slide ID "DS1" is "/data/hogel".

The slide data storage unit 122 stores information regarding slide data for the slides imaged by the first imaging device 10. Here, FIG. 8 illustrates an example of the slide data storage unit 122 according to the embodiment. As illustrated in FIG. 8, the slide data storage unit 122 includes items such as "slide ID" and "slide data".

The "slide ID" indicates identification information for identifying a slide. The "slide data" indicates information regarding the slide data. For example, the "slide data" indicates a pathological image obtained by imaging a slide, information regarding the slide, and the like. In the example of FIG. 8, it is illustrated that conceptual information such as "slide data #1" and "slide data #2" is stored in the "slide data". However, data such as a pathological image is actually stored. In the example of FIG. 8, it is illustrated that the slide data for the slide identified by the slide ID "DS1" is "slide data #1".

Figures 9, 10:
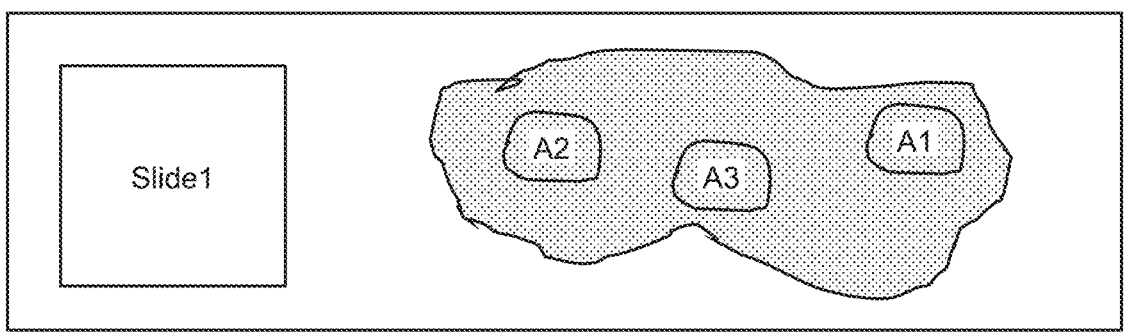
FIG. 9 is a diagram illustrating an example of an annotation storage unit according to the embodiment.
FIG. 10 is a diagram illustrating an example of a pathological subject according to the embodiment.

The annotation storage unit 123 stores information regarding annotations of the slides imaged by the first imaging device 10. Here, FIG. 9 illustrates an example of the annotation storage unit 123 according to the embodiment. As illustrated in FIG. 9, the annotation storage unit 123 includes items such as "annotation ID", "slide ID", "annotation data", and "label".

The "annotation ID" indicates identification information for identifying an annotation. The "slide ID" indicates identification information for identifying a slide. The "slide ID" indicates identification information for identifying a slide to which the annotation is attached. The "annotation data" indicates information regarding the annotation data. For example, the "annotation data" indicates position information for the annotation, additional information for the annotation, and the like. In the example of FIG. 9, it is illustrated that coordinate information such as "A1_1.xml" and "A2_1.xml" is stored in the "annotation data" in XML format. The "label" indicates information regarding labels added to the annotations. In the example of FIG. 9, it is illustrated that a label added to an annotation identified by the annotation ID "DA1" and the slide ID "DS1" is "cancer". As described above, the "label" is a label indicating, for example, whether a corresponding site is cancer, non-cancer, and indicates learning data generated for learning.

FIG. 10 is an example of the information illustrated in FIG. 9. A slide 1 illustrated in FIG. 10 corresponds to the slide identified as DS1 in FIG. 9. A1 to A3 illustrated in FIG. 10 correspond to the annotations identified as A1_1.xml to A3_1.xml in FIG. 9. As described above, a plurality of annotations may be included in one slide. In this case, the annotations can be identified on the basis of the annotations ID and the slide ID.

The new slide storage unit 124 stores information regarding slides imaged by the second imaging device 20. Here, FIG. 11 illustrates an example of the new slide storage unit 124 according to the embodiment. The new slide storage unit 124 stores the same information as the slide storage unit 121. Therefore, description thereof will be omitted.

The new slide data storage unit 125 stores information regarding slide data for the slides imaged by the second imaging device 20. Here, FIG. 12 illustrates an example of the new slide data storage unit 125 according to the embodiment. The new slide data storage unit 125 stores the same information as the slide data storage unit 122. Therefore, description thereof will be omitted.

The transcription annotation storage unit 126 stores information regarding annotations after transcription. The transcription annotation storage unit 126 stores information regarding annotations after the annotations of the slides imaged by the first imaging device 10 are converted. The transcription annotation storage unit 126 stores information regarding annotations after the annotations stored in the annotation storage unit 123 are converted. Here, FIG. 13 illustrates an example of the transcription annotation storage unit 126 according to the embodiment. The transcription annotation storage unit 126 stores the same information as the annotation storage unit 123. Therefore, description thereof will be omitted.

The correction annotation storage unit 127 stores information regarding correction annotations. The correction annotation storage unit 127 stores information regarding correction annotations generated on the basis of the information regarding the transcription annotations and the new slide data. For example, the correction annotation storage unit 127 stores information regarding correction annotations after adsorption fitting based on the information regarding the transcription annotations and the new slide data. Here, FIG. 14 illustrates an example of the correction annotation storage unit 127 according to the embodiment. As illustrated in FIG. 14, the correction annotation storage unit 127 includes items such as "correction annotation ID", "new slide data", "transcription annotation data", and "label".

The "correction annotation ID" indicates identification information for identifying a correction annotation. The "new slide data" indicates information regarding the new slide data. The "transcription annotation data" indicates information regarding the transcription annotation data. The "label" indicates information regarding labels added to the original annotations.

The model storage unit 128 stores information regarding models. For example, the model storage unit 128 stores information regarding models that output information indicating a degree of diagnosis with respect to a pathological subject. For example, the model storage unit 128 stores information regarding models that output information indicating a degree of diagnosis based on the new slide data and the correction annotations. FIG. 15 illustrates an example of the model storage unit 128. As illustrated in FIG. 15, the model storage unit 128 includes items such as "model ID" and "model (calculation formula)".

The "model ID" indicates identification information for identifying a model. The "model (calculation formula)" indicates a calculation formula for the model. In the example of FIG. 15, it is illustrated that conceptual information such as "model #11" and "model #22" is stored in the "model (calculation formula)". However, a weight for the model is actually stored. For example, a weight for connection between nodes in a neural network is stored in the "model (calculation formula)".

The coordinate conversion information storage unit 129 stores information regarding conversion of annotation using the coordinate information. FIG. 16 illustrates an example of the coordinate conversion information storage unit 129. As illustrated in FIG. 16, the coordinate conversion information storage unit 129 includes items such as "coordinate conversion ID" and "coordinate conversion information".

The "coordinate conversion ID" indicates identification information for identifying coordinate conversion information. The "coordinate conversion information" indicates information regarding coordinate information for converting an annotation in the format of the first imaging device 10 into that in the format of the second imaging device 20.

Figures 17, 18:
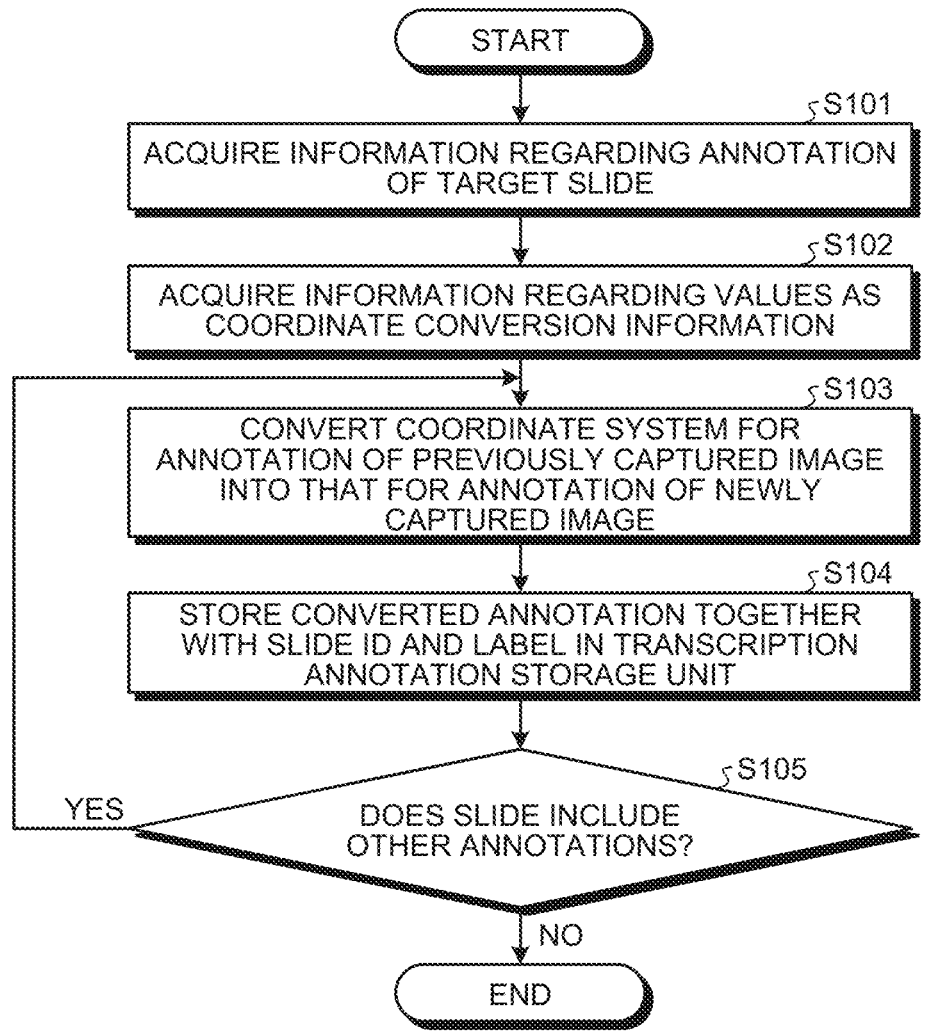
FIG. 17 is a diagram illustrating an example of a coordinate conversion information according to the embodiment.
FIG. 18 is a flowchart illustrating an example of information processing according to the embodiment.

FIG. 17 illustrates an example of the coordinate conversion information. For example, FIG. 17 illustrates an example of "coordinate conversion #11" illustrated in FIG. 16 as the coordinate conversion information. FIG. 17 illustrates values held in the coordinate conversion information. FIG. 17 illustrates a case where values by the first imaging device 10, which is previously used for capturing images, and values by the second imaging device 20 are held. FIG. 17 illustrates a case where the imaging values are based on um/pix indicating how many um one pixel corresponds to. FIG. 17 illustrates a case where two-axis values are held because values may be different on the vertical and horizontal axes. FIG. 17 illustrates a case where the format of the first imaging device 10 is converted into the format of the second imaging device 20, by converting the coordinate information on the vertical axis from 5 um/pix, which is a value in a previously captured image, to 2 um/pix, which is a value in a newly captured image, and converting the coordinate information on the horizontal axis from 10 um/pix, which is a value in the previously captured image, to 5 um/pix, which is a value in the newly captured image.

(Control Unit 130)

The control unit 130 is a controller, and is realized by, for example, a CPU, an MPU, or the like executing various programs stored in a storage device inside the generation device 100 using a RAM as a work area. Alternatively, the control unit 130 is a controller, and is realized by, for example, an integrated circuit such as an ASIC or an FPGA.

As illustrated in FIG. 6, the control unit 130 includes an acquisition unit 131, a conversion unit 132, an adsorption unit 133, a generation unit 134, and a provision unit 135 to realize or execute information processing to be described below. Note that the internal configuration of the control unit 130 is not limited to the configuration illustrated in FIG. 6, and may be another configuration as long as the information processing to be described later is performed.

(Acquisition Unit 131)

The acquisition unit 131 acquires first pathological images captured by the first imaging device 10. Referring to the example illustrated in FIG. 1, the acquisition unit 131 acquires the first pathological images stored in the server 11.

The acquisition unit 131 acquires annotations added to the first pathological images. Referring to the example illustrated in FIG. 1, the acquisition unit 131 acquires the annotations stored in the server 11. Then, the acquisition unit 131 stores the acquired annotations in the annotation storage unit 123. Then, the acquisition unit 131 stores slide IDs corresponding to the acquired first pathological images in the slide storage unit 121. In addition, the acquisition unit 131 stores the acquired slide data in the slide data storage unit 122.

The acquisition unit 131 acquires coordinate conversion information for converting the annotation of the first pathological image to correspond to the second pathological image. For example, the acquisition unit 131 acquires coordinate conversion information for converting the coordinate information for the first pathological image into the coordinate information for the second pathological image from the coordinate conversion information storage unit 129.

The acquisition unit 131 acquires second pathological images. The acquisition unit 131 acquires second pathological images captured by the second imaging device 20. Referring to the example illustrated in FIG. 1, the acquisition unit 131 acquires the second pathological images stored in a server 21. Then, the acquisition unit 131 stores slide IDs corresponding to the acquired second pathological images in the new slide storage unit 124. In addition, the acquisition unit 131 stores the acquired second pathological images in the new slide data storage unit 125.

The acquisition unit 131 acquires transcription annotations. For example, the acquisition unit 131 acquires transcription annotations from the transcription annotation storage unit 126. For example, the acquisition unit 131 acquires the transcription annotations with the second pathological images.

The acquisition unit 131 acquires correction annotations. For example, the acquisition unit 131 acquires correction annotations from the correction annotation storage unit 127. For example, the acquisition unit 131 acquires the correction annotations with the second pathological images.

The acquisition unit 131 acquires learning models. For example, the acquisition unit 131 acquires learning models from the model storage unit 128. For example, in a case where a first pathological image is diagnosed, the acquisition unit 131 acquires the learning model M1. For example, in a case where a second pathological image is diagnosed, the acquisition unit 131 acquires the learning model M2.

(Conversion Unit 132)

The conversion unit 132 converts the annotation added to the first pathological image, which is acquired by the acquisition unit 131. The conversion unit 132 converts the annotation added to the first pathological image into that corresponding to the second pathological image using the coordinate conversion information acquired by the acquisition unit 131. In this way, the conversion unit 132 generates a transcription annotation. Then, the conversion unit 132 stores the transcription annotation in the transcription annotation storage unit 126.

The conversion unit 132 converts the coordinate information for the annotation corresponding to the previously captured pathological image into that for an annotation corresponding to a newly captured pathological image. As a specific example, the annotation corresponding to the previously captured pathological image is a square mark, and the coordinate information for vertexes of the square is (0, 0), (0, 100), (100, 0), and (100, 100), respectively. Meanwhile, in FIG. 16, a combination of the first imaging device 10 and the second imaging device 20 is associated with "DX11" in advance. In this case, when the combination of the first imaging device 10 and the second imaging device 20 is input, the conversion unit 132 converts the coordinate information using the coordinate conversion information corresponding to "DX11" stored in the coordinate conversion information storage unit 129. Here, in a case where the coordinate conversion information corresponding to "DX11" is the coordinate conversion information illustrated in FIG. 17, pixel marks (0, 0), (0, 100), (100, 0), and (100, 100) are expressed in micrometer marks as (0, 0), (0, 500), (1000, 0), and (1000, 500), respectively. Then, the conversion unit 132 converts the coordinate information into that for the annotation corresponding to the newly captured pathological image using the coordinate conversion information illustrated in FIG. 17, i.e. (0, 0), (0, 500/2), (1000/5, 0), and (1000/5, 500/2), respectively. In this way, the conversion unit 132 converts the coordinate information into that for the annotation corresponding to the newly captured pathological image.

(Adsorption Unit 133)

The adsorption unit 133 transcribes the transcription annotation generated by the conversion unit 132 to the second pathological image. For example, the adsorption unit 133 transcribes the transcription annotation stored in the transcription annotation storage unit 126 to the second pathological image stored in the new slide data storage unit 125. Specifically, the adsorption unit 133 transcribes the transcription annotation acquired from the transcription annotation storage unit 126 by the acquisition unit 131 to the second pathological image acquired from the new slide data storage unit 125 by the acquisition unit 131.

The adsorption unit 133 performs adsorption fitting processing on the transcription annotation transcribed to the second pathological image. In this way, the adsorption unit 133 generates a correction annotation. Then, the adsorption unit 133 stores the correction annotation in the correction annotation storage unit 127.

(Generation Unit 134)

The generation unit 134 generates a learning model M2 that estimates pathological information for the second pathological image. When the second pathological image is input, the generation unit 134 generates a learning model M2 that outputs information for estimating pathological information for the second pathological image. The generation unit 134 generates a learning model M2 that estimates pathological information for the second pathological image using the correction annotations as learning data. For example, the generation unit 134 generates a learning model M2 that estimates pathological information. For example, the generation unit 134 generates a learning model M2 that estimates a probability that a region including a lesion is included in the second pathological image. Then, the generation unit 134 stores the generated learning model M2 in the model storage unit 128.

The generation unit 134 may generate a learning model M2 that estimates pathological information for the second pathological image using the transcription annotations as learning data. For example, the adsorption fitting processing is not performed in such a case. The generation unit 134 stores the generated learning model M2 in the model storage unit 128.

The generation unit 134 may generate a learning model M1 that estimates pathological information for the first pathological image using the annotations as learning data. For example, the learning model M1 is used for diagnosing a first pathological image in such a case. The generation unit 134 stores the generated learning model M1 in the model storage unit 128.

(Provision Unit 135)

The provision unit 135 provides a learning model generated by the generation unit 134. For example, the provision unit 135 provides a learning model generated by learning the correction annotations. For example, the provision unit 135 provide a learning model that estimates pathological information for the second pathological image when the second pathological images captured by the second imaging device 20 is input.

[5. Flow of Information Processing]

Figure 19:
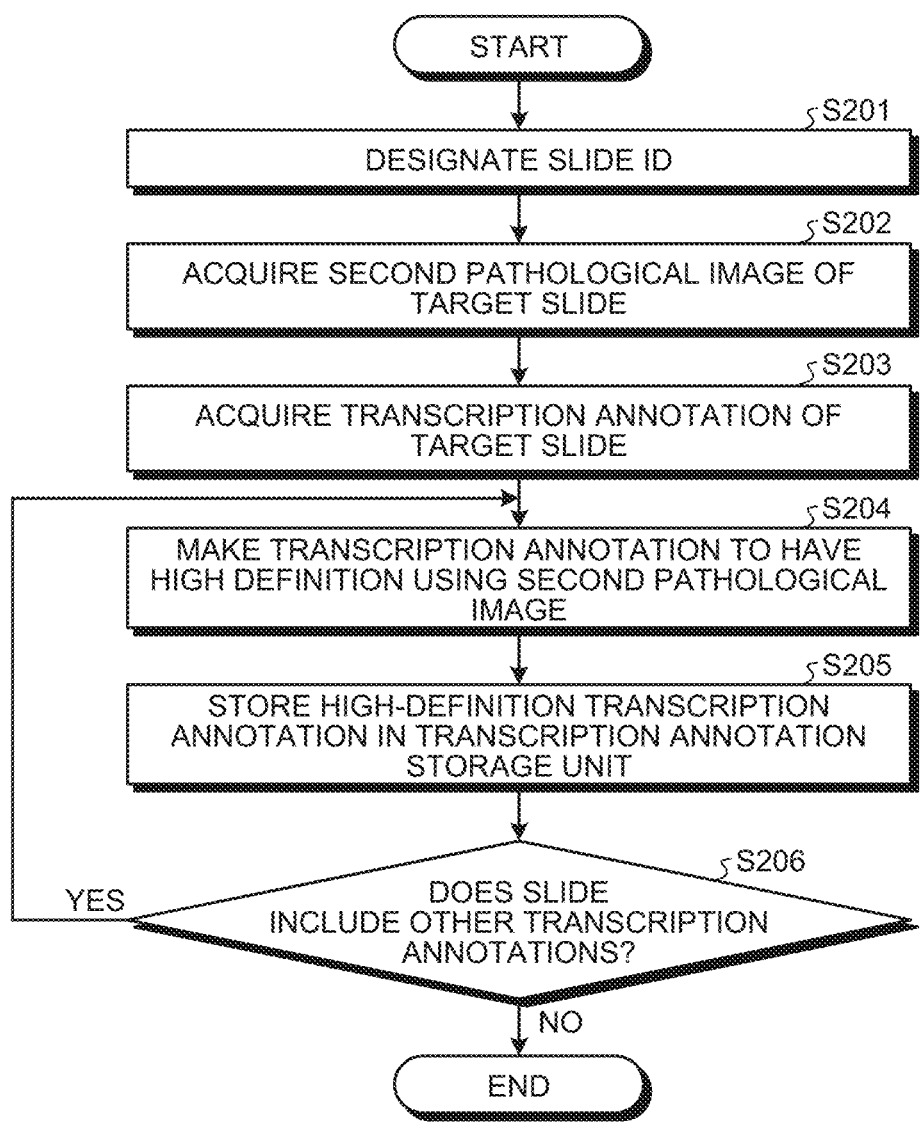
FIG. 19 is a flowchart illustrating an example of information processing according to the embodiment.
Figure 20:
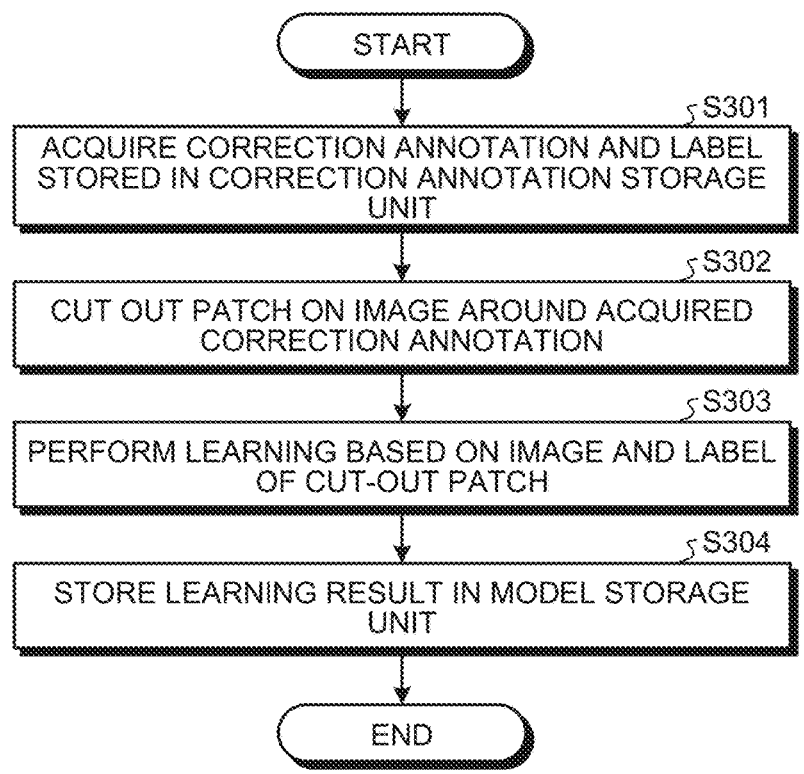
FIG. 20 is a flowchart illustrating an example of information processing according to the embodiment.

Next, a process of information processing by the information processing system 1 according to the embodiment will be described with reference to FIGS. 18 to 20. FIGS. 18 to 20 are flowcharts illustrating a process of information processing by the information processing system 1 according to the embodiment.

As illustrated in FIG. 18, the generation device 100 acquires information regarding an annotation of a target slide (step S101). The generation device 100 acquires information regarding values as coordinate conversion information (step S102). The generation device 100 converts coordinate information for the annotation of the previously captured image into that for the annotation of the captured image (step S103). The generation device 100 stores the converted annotation together with a slide ID and a label in the transcription annotation storage unit 126 (step S104). The generation device 100 estimates whether the slide includes other annotations (step S105). When the slide includes other annotations (step S105; YES), the generation device 100 repeats the processing of steps S103 and S104 as many as the number of other annotations included in the slide. On the other hand, when the slide includes no other annotations (step S105; NO), the generation device 100 ends the information processing.

An example of processing of the generation unit 134 will be described with reference to FIG. 19. FIG. 19 illustrates processing in which the generation device 100 converts the transcription annotation into that based on higher-definition coordinates using a second pathological image when the image is recognized. As illustrated in FIG. 19, a slide ID is designated to the generation device 100 (step S201). The generation device 100 acquires a second pathological image of a target slide (step S202). The generation device 100 acquires a transcription annotation of the target slide (step S203). The generation device 100 makes the acquired transcription annotation to have a high definition using the second pathological image (step S204). Here, the generation device 100 may use, for example, graph cut, as processing for the high definition. For example, the generation device 100 may use a method described in U.S. Pat. No. 8,787,642 B2 or the like as the processing for the high definition. The generation device 100 stores the high-definition correction annotation in the correction annotation storage unit 127 (step S205). In addition, the generation device 100 stores a label added together with the annotation as a label of the correction annotation in the correction annotation storage unit 127. The generation device 100 estimates whether the slide includes other transcription annotations (step S206). When the slide includes other transcription annotations (step S206; YES), the generation device 100 repeats the processing of steps S204 and S205 as many as the number of other transcription annotations included in the slide. On the other hand, when the slide includes no other transcription annotations (step S206; NO), the generation device 100 ends the information processing.

An example of processing of the generation unit 134 will be described with reference to FIG. 20. As illustrated in FIG. 20, the generation device 100 acquires the correction annotation and the label stored in the correction annotation storage unit 127 (step S301). The generation device 100 cuts out a patch on the image around the acquired correction annotation (step S302). Here, the patch may have any size. The generation device 100 generates a learning model M2 by learning the image and the label of the cut-out patch (step S303). The generation device 100 stores the generated learning model M2 in the model storage unit 128 (step S304).

[6. Variation on Processing]

The information processing system 1 according to the above-described embodiment may be implemented in various different modes other than the above-described embodiment. Hereinafter, other embodiments of the information processing system 1 will be described. Note that the same description as that for the above-described embodiment will be appropriately omitted.

[6-1. Type of Label]

It has been described in the example described above that the label according to the embodiment is provided for each annotation, but the label may be provided for each target slide. For example, in the above-described embodiment, in a case where only one annotation is included in a slide, the label according to the embodiment may be provided for each slide. In addition, the label according to the embodiment may be provided for each target pathological image. For example, in the above-described embodiment, in a case where only one annotation is included in a pathological image obtained by imaging a slide, the label according to the embodiment may be provided for each pathological image.

[6-2. Provision of Estimation Result]

In the above-described example, it has been described that the generation device 100 provides the learning model M2 to the server 11. Here, the generation device 100 may provide an estimation result to the server 11 by receiving a second pathological image from the server 11. For example, when receiving a second pathological image from the server 11, the generation device 100 acquires the learning model M2 corresponding to the second pathological image from the model storage unit 128. Then, the generation device 100 inputs the second pathological image to the learning model M2 to estimate pathological information for the second pathological image. In addition, the generation device 100 labels a correction annotation on the basis of the estimation result. Then, the generation device 100 transmits the pathological estimation result for the second pathological image to the server 11. In this case, the server 11 transmits the received estimation result to the display control device 12. The display control device 12 controls the display device 13 to display the estimation result received from the server 11. Although not illustrated in FIG. 6, the generation device 100 may include an estimation unit 137. The estimation unit 137 inputs the second pathological image acquired by the acquisition unit 131 to the learning model M2 to estimate pathological information for the second pathological image. In a case where the estimation unit 137 is included in the generation device 100, the provision unit 135 provides the estimation result estimated by the estimation unit 137 to the server 11.

[6-3. Learning Method]

The learning model according to the embodiment is not limited to a model based on a neural network such as a deep learning model, and any model may be applicable as long as the model is based on a machine learning algorithm. For example, the learning model may be a model based on random forest.

[6-4. Pathological Subject]

It has been described in the example described above that the pathological subject according to the embodiment is a section of a cell, a tissue, an organ, or the like of a living body, but any pathological subject may be applicable as long as the pathological subject is collected from a patient. For example, the pathological subject according to the embodiment may be blood or the like.

[6-5. Imaging Subject]

In the example described above, it has been described that the pathological subject imaged by the first imaging device 10 and the pathological subject imaged by the second imaging device 20 are the same section of the same tissue, cell, organ, or the like. That is, in the example described above, it has been described that the slide imaged by the first imaging device 10 and the slide imaged by the second imaging device 20 are the same one. Here, the slide imaged by the first imaging device 10 and the slide imaged by the second imaging device 20 may not be the same one. Specifically, the pathological subject imaged by the first imaging device 10 and the pathological subject imaged by the second imaging device 20 may be different sections collected from the same tissue, cell, organ, or the like. For example, the pathological subject imaged by the first imaging device 10 and the pathological subject imaged by the second imaging device 20 may be different tissues collected from the same tissue block. In addition, the same section of the same tissue, cell, organ, or the like for the pathological subject includes a pathological subject in a deteriorating state to some extent as a predetermined period elapses or the like. Here, the deteriorating state to some extent may be any state as long as a difference in the feature amount on the pathological image at the imaging time between the state after the deterioration and the state before deterioration is smaller than a predetermined threshold.

[6-6. Annotation Conversion Method Using Coordinate Information]

In the example described above, it has been described that an annotation of one pathological image is converted on the basis of coordinate information for two pathological images. Here, the coordinate information according to the embodiment may be determined in any way as long as the coordinate information corresponds to the slide. For example, the coordinate information according to the embodiment may be coordinate information defined with a specific position on the slide as the origin. For example, the coordinate information according to the embodiment may be coordinate information defined with one of the four corners of the slide as the origin.

Furthermore, the conversion according to the embodiment may be conversion for correcting a deviation, such as because the slide moves according to a stage movement specification of the imaging device or the entire slide is inclined. Specifically, the movement of the slide according to a stage movement specification of the imaging device or the like may cause a difference in position between the previously captured pathological image and the newly captured pathological image. In this case, the generation device 100 corrects a deviation of the pathological image on the basis of image recognition processing. For example, the generation device 100 corrects the deviation of the pathological image on the basis of processing such as feature point extraction or template matching. Furthermore, the conversion according to the embodiment is not limited to these examples, and may be conversion for correcting a deviation caused by lens distortion. Furthermore, the lens distortion correction may be correction to the entire slide by capturing images multiple times and integrating the captured images. In this case, the generation device 100 may perform lens distortion correction to the entire slide by performing lens distortion correction on each of the plurality of captured pathological images and integrating the plurality of pathological images on which the lens distortion correction has been performed. Furthermore, the lens distortion correction is not limited to correction to the entire slide, and may be local correction.

[6-7. Annotation Conversion Method Using Format of Imaging Device]

In the example described above, it has been described that the annotation added in the first imaging device 10 is converted into that in a format of the second imaging device 20, on the basis of the coordinate information for the pathological image captured by the first imaging device 10 and the coordinate information for the pathological image captured by the second imaging device 20. Here, the conversion of the annotation according to the embodiment is not limited to the conversion using the coordinate information. For example, the conversion of the annotation according to the embodiment may be conversion based on a format in which the pathological image is stored. In this case, in a case where the format in which the first pathological image is stored is different from the format in which the second pathological image is stored, the generation device 100 converts the annotation added to the first pathological image to correspond to the format in which the second pathological image is stored. For example, the generation device 100 converts the annotation to correspond to the format of the second pathological image by associating the format using conversion information determined in advance.

[6-8. Annotation According to Embodiment]

The annotation according to the embodiment may be any information as long as the information is added onto the image. The annotation according to the embodiment may be information added by object recognition using machine learning or the like, or may be information manually added by a user. Note that the annotation according to the embodiment is not limited to a closed curve, and may be a non-closed ring. Furthermore, the annotation according to the embodiment may have any geometric shape. Furthermore, the annotation according to the embodiment may include information visualized on the image in the process of generating the annotation. For example, the annotation according to the embodiment may include information regarding annotation fitting based on feature information on the image. For example, the annotation according to the embodiment may include information regarding annotation fitting conditions.

The label according to the embodiment may be any one as long as the label is intended for medical or pathological information. For example, the label according to the embodiment is a label indicating a condition of a cell, tissue, organ, or the like of a patient's living body. As a specific example, the label indicates cancer. In addition, the label according to the embodiment may be a label indicated by binary classification such as whether or not it is cancer. Specifically, the label according to the embodiment may be a label such as "cancer" or "non-cancer". In addition, the label according to the embodiment may be, for example, a label indicating a detailed classification of cancer. Specifically, the label according to the embodiment may be a label indicating a progression stage of cancer, such as "stage 1", "stage 2", or "stage 3", or may be a label indicating the type of cancer, such as "esophageal cancer", "colorectal cancer", or "gastric cancer". In addition, the label according to the embodiment is provided for each annotation. Note that, in the embodiment, a plurality of labels may be added to one annotation. For example, in the embodiment, a plurality of labels such as "cancer", "stage 1", and "esophageal cancer" may be added to one annotation. Note that, in the embodiment, an annotation to which no label is added may be considered as being given a label indicating no abnormality.

[6-9. Slide According to Embodiment]

The slide according to the embodiment may be any one as long as the slide is a general slide used in a microscope. For example, the slide according to the embodiment is a glass slide. In the above-described embodiment, the slide may be mentioned as "glass slide" or "pathological slide".

[6-10. Conversion of Annotation]

In the example described above, it has been described that the annotation is transcribed on the basis of the coordinate information for the first pathological image and the coordinate information for the second pathological image. In addition, the present embodiment is not limited to the transcription of the annotation based on the coordinate information. For example, the generation device 100 may transcribe the annotation on the basis of feature points of the first pathological image and the second pathological image. Specifically, the generation device 100 extracts a feature point of the first pathological image and a feature point of the second pathological image. Then, the generation device 100 matches the first pathological image and the second pathological image such that the feature points extracted from the respective pathological images match each other. In this way, the generation device 100 generates conversion information for matching the first pathological image and the second pathological image on the basis of the feature point of the first pathological image and the feature point of the second pathological image. Then, the generation device 100 transcribes the annotation according to the conversion information.

[6-11. Learning Data]

In the example described above, it has been described that the learning data for estimating pathological information for the second pathological image is generated on the basis of the conversion of the annotation using the coordinate information and the adsorption fitting. Here, the generation device 100 may generate the learning model M2 using the transcription annotation as learning data. That is, the generation device 100 may not perform adsorption fitting processing.

[6-12. Identification of Slide Using Pathological Case Number]

In the example described above, it has been assumed that a slide ID, which can uniquely identify a slide, is printed on a label or the like. However, in each hospital, the label and the slide ID may be managed in a different way, and a slide may be held in an ID form that is not capable of uniquely identifying the slide. For example, as one of the most typical ways, the slide ID is managed on a pathological case number basis. In this case, the ID is managed based on the pathological case number. In addition, the pathological case number may also include a plurality of slides. Therefore, even if the pathological case number can be identified by recognizing the label, it is not always possible to identify the slides.

Figure 21:
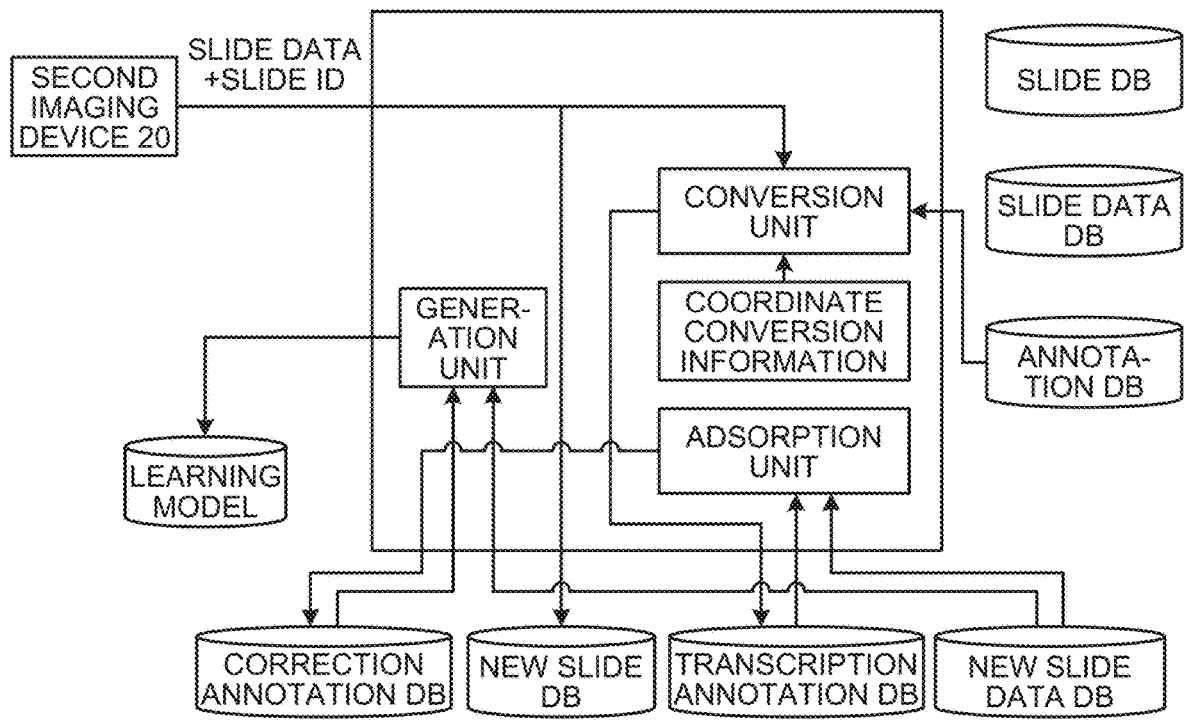
FIG. 21 is a diagram illustrating a configuration example and a flow of the generation device according to the embodiment.
Figure 22:
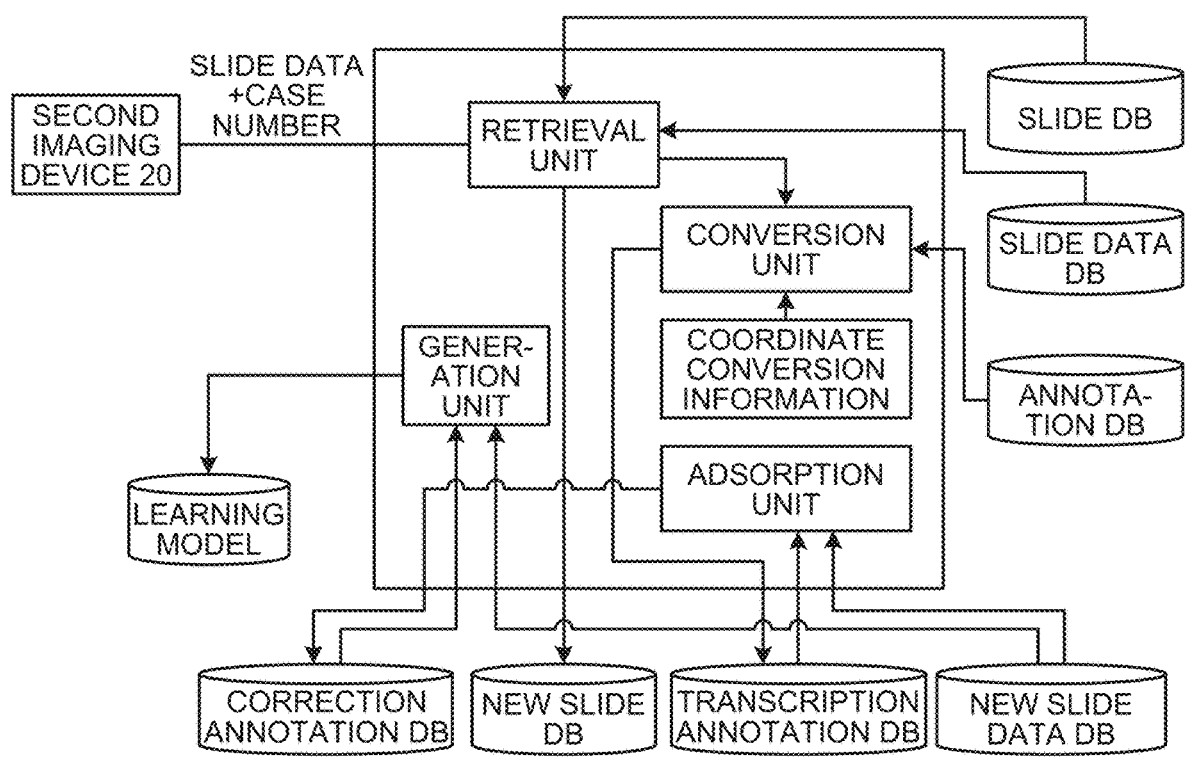
FIG. 22 is a diagram illustrating a configuration example and a flow of a generation device according to a modification.
Figure 23:
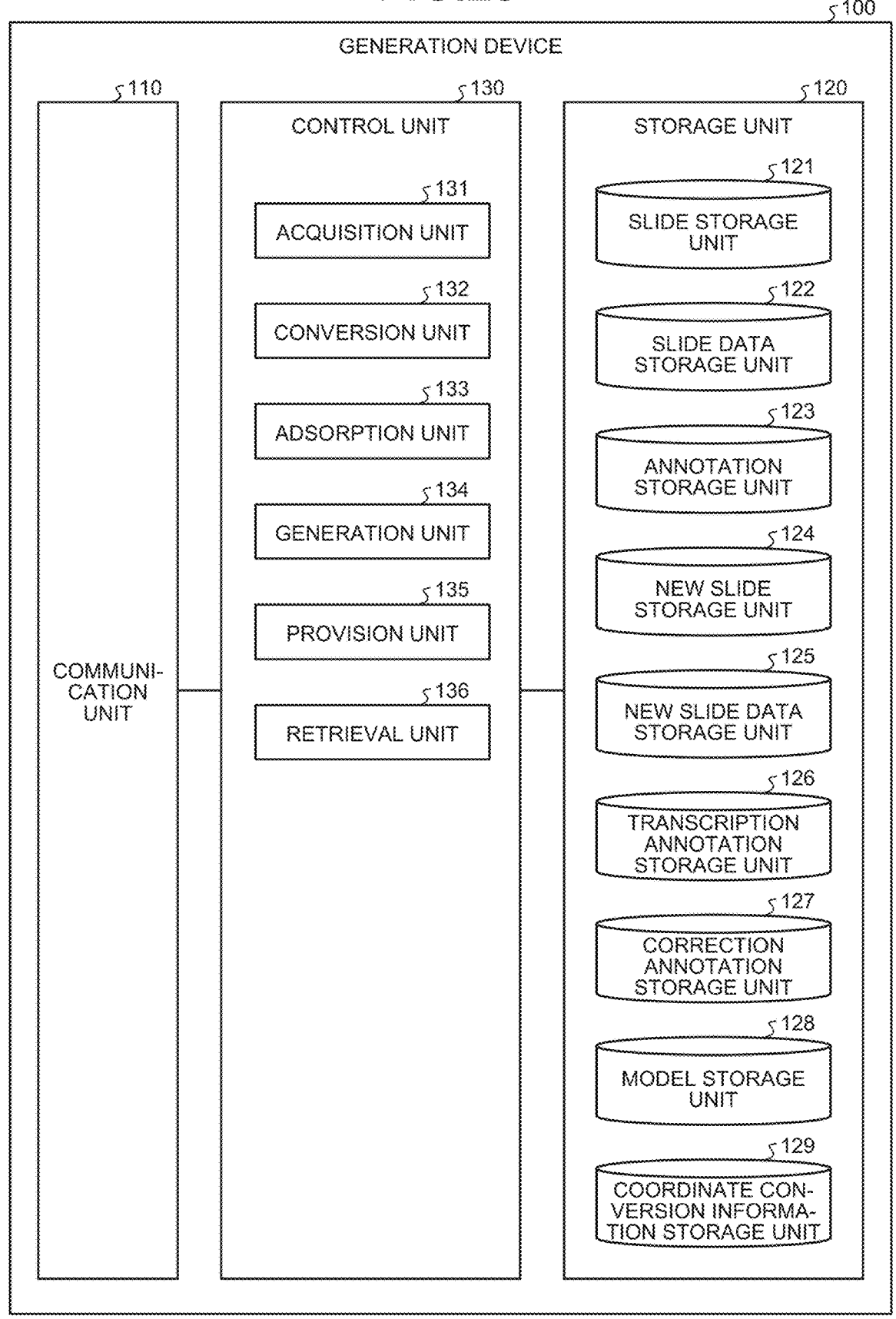
FIG. 23 is a diagram illustrating a configuration example of the generation device according to the modification.

Hereinafter, processing of identifying a slide in a case where the slide is held in an ID form that is not capable of uniquely identifying the slide will be described. In the modification, information processing for identifying a slide by performing image processing is added. Specifically, in the modification, a retrieval unit 136 identifying a slide is added. FIG. 22 illustrates an overall configuration diagram for the information processing according to the modification. Note that processing other than the information processing by the retrieval unit 136 is the same as that in the example illustrated in FIG. 21, and thus, description thereof will be omitted. As illustrated in FIG. 23, the control unit 130 may include a retrieval unit 136. Furthermore, the control unit 130 may realize or execute information processing to be described below.

(Retrieval Unit 136)

The retrieval unit 136 identifies a slide for the first pathological image. The retrieval unit 136 identifies a slide corresponding to the pathological case number. Specifically, the retrieval unit 136 identifies the same slide as that for the second pathological image on the basis of image processing. For example, the retrieval unit 136 identifies a slide using a technique such as histogram matching, feature point extraction, template matching, or the like between the pathological images. In addition, the retrieval unit 136 may identify a slide for a first pathological image having a high degree of similarity by calculating a degree of similarity between the pathological images using machine learning.

Figure 24:
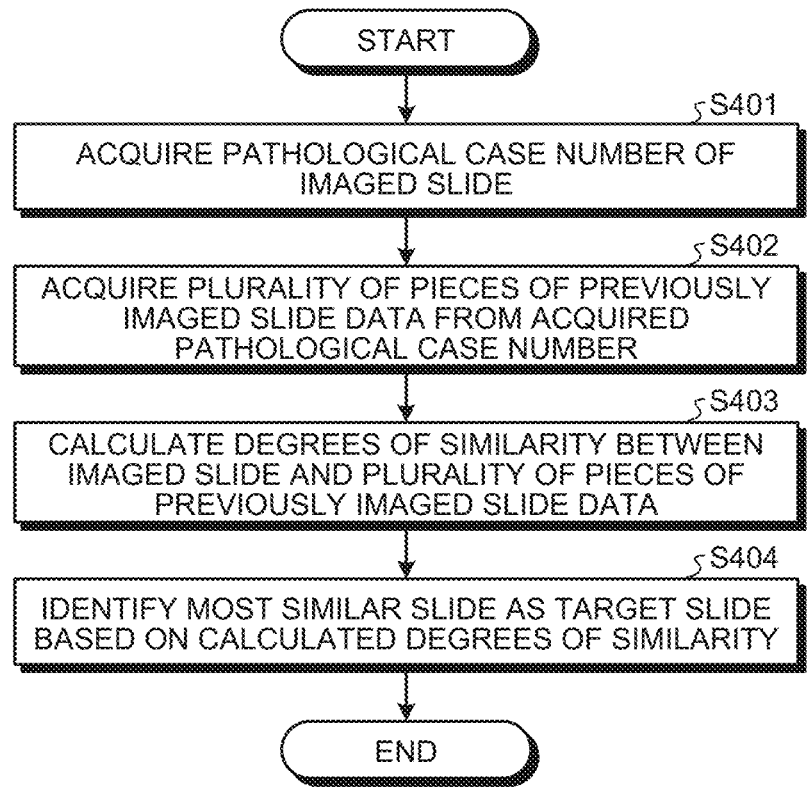
FIG. 24 is a flowchart illustrating an example of information processing according to the modification.

Next, a process of information processing by the information processing system 1 according to the modification will be described with reference to FIG. 24. FIG. 24 is a flowchart illustrating a process of information processing by the information processing system 1 according to the embodiment.

As illustrated in FIG. 24, the generation device 100 acquires a pathological case number of a slide (step S401). The generation device 100 acquires a plurality of pieces of previously imaged slide data from the acquired pathological case number (step S402). The generation device 100 calculates degrees of similarity between an imaged slide and the plurality of pieces of previously imaged slide data (step S403). The generation device 100 identifies a slide having the highest degree of similarity based on the calculated degrees of similarity (step S404).

[7. Hardware Configuration]

Figure 25:
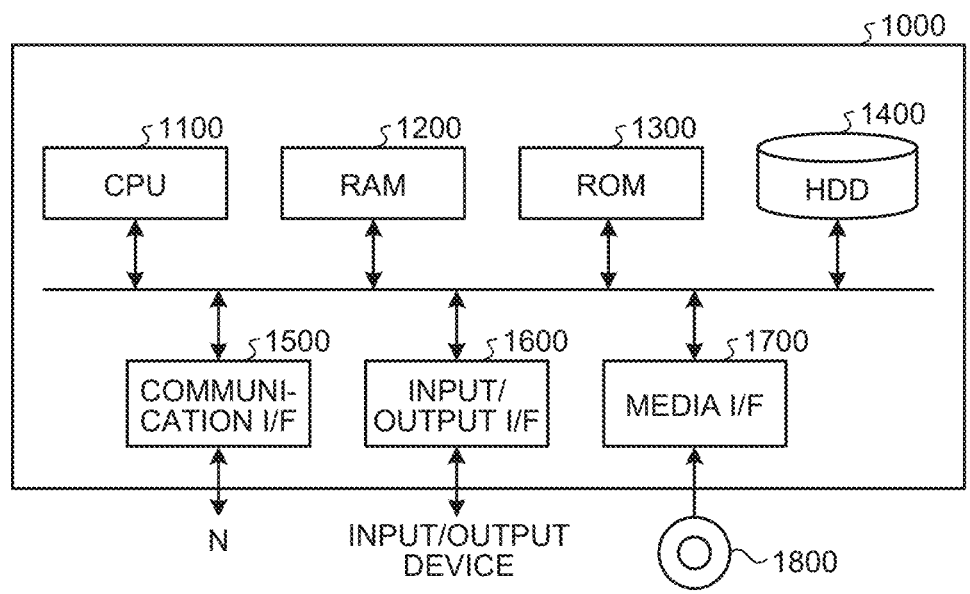
FIG. 25 is a hardware configuration diagram illustrating an example of a computer realizing functions of the generation device.

Furthermore, the imaging system 2 and the generation device 100 according to the above-described embodiment are realized by, for example, a computer 1000 having a configuration as illustrated in FIG. 25. FIG. 25 is a hardware configuration diagram illustrating an example of a computer realizing the functions of the imaging system 2 and the generation device 100. The computer 1000 includes a CPU 1100, a RAM 1200, a ROM 1300, an HDD 1400, a communication interface (I/F) 1500, an input/output interface (I/F) 1600, and a media interface (I/F) 1700.

The CPU 1100 operates on the basis of a program stored in the ROM 1300 or the HDD 1400 to control each unit. The ROM 1300 stores a boot program executed by the CPU 1100 when the computer 1000 is activated, a program depending on hardware of the computer 1000, and the like.

The HDD 1400 stores a program executed by the CPU 1100, data used by the program, and the like. The communication interface 1500 receives data from another device via a predetermined communication network, sends the data to the CPU 1100, and transmits data generated by the CPU 1100 to another device via the predetermined communication network.

The CPU 1100 controls an output device such as a display or a printer and an input device such as a keyboard or a mouse via the input/output interface 1600. The CPU 1100 acquires data from the input device via the input/output interface 1600. Also, the CPU 1100 outputs generated data to the output device via the input/output interface 1600.

The media interface 1700 reads out a program or data stored in a recording medium 1800 and provides the program or data to the CPU 1100 via the RAM 1200. The CPU 1100 loads the program from the recording medium 1800 onto the RAM 1200 via the media interface 1700, and executes the loaded program. The recording medium 1800 is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, in a case where the computer 1000 functions as the imaging system 2 and the generation device 100 according to the embodiment, the CPU 1100 of the computer 1000 realizes the function of each control unit by executing the programs loaded on the RAM 1200. The CPU 1100 of the computer 1000 reads out the programs from the recording medium 1800 and executes the read-out programs, but as another example, the programs may be acquired from another device via the predetermined communication network.

[8. Others]

In addition, in the processes described in the above-described embodiments and modifications, all or some of the processes described as being automatically performed can be manually performed, or all or some of the processes described as being manually performed can be automatically performed by known methods. In addition, the processing procedure, the specific terms, and the information including various kinds of data and parameters disclosed above and in the drawings can be arbitrarily changed unless otherwise specified. For example, the various types of information illustrated in each of the drawings are not limited to the illustrated information.

In addition, each component of each device illustrated in the drawings is conceptual in functional term, and is not necessarily configured as illustrated in the drawings in physical term. That is, a specific form in which the devices are distributed or integrated is not limited to what is illustrated, and all or some of the devices can be functionally or physically distributed or integrated in an arbitrary unit according to various loads, usage conditions, and the like.

In addition, the above-described embodiments and modifications can be appropriately combined if no contradiction in processing is caused.

Although some of the embodiments of the present application have been described in detail with reference to the drawings, these embodiments are merely exemplary, and the present invention can be implemented in other forms with various modifications and improvements based on the knowledge of those skilled in the art, as well as according to the embodiments described above.

In addition, the "section", "module", or "unit" described above can be interpreted as "means", "circuit", or the like. For example, the acquisition unit can be interpreted as an acquisition means or an acquisition circuit.

Note that the present technology can also have the following configurations.

(1)

A generation device comprising:
an acquisition unit that acquires a first pathological image captured, and an annotation that is information added to the first pathological image and is meta information related to the first pathological image; and
a generation unit that generates learning data for evaluating pathological-related information based on a second pathological image according to the second pathological image different from the first pathological image, the learning data being learning data obtained by transcribing the annotation in a manner corresponding to the second pathological image.

(2)

The generation device according to (1), wherein
the generation unit
after converting the annotation into an annotation corresponding to the second pathological image, generates the learning data obtained by transcribing the converted annotation.

(3)

The generation device according to (1) or (2), wherein
the generation unit
generates the learning data on the basis of the second pathological image that is a pathological image having a different resolution from a resolution of the first pathological image.

(4)

The generation device according to any one of (1) to (3), wherein
the generation unit
generates the learning data on the basis of the second pathological image that is a pathological image having higher visibility than visibility of the first pathological image.

(5)

The generation device according to any one of (1) to (4), wherein the generation unit generates the learning data on the basis of the second pathological image that is a pathological image having a lower resolution than resolution of the first pathological image.

(6)

The generation device according to any one of (1) to (5), wherein the generation unit generates the learning data on the basis of the second pathological image that is a pathological image captured under a different imaging condition from an imaging condition of the first pathological image.

(7)

The generation device according to any one of (1) to (6), wherein the generation unit generates the learning data on the basis of the second pathological image that is a pathological image captured by a different imaging device from an imaging device that has captured the first pathological image.

(8)

The generation device according to any one of (1) to (7), wherein the generation unit generates the learning data on the basis of the second pathological image that is a pathological image captured at a different magnification from a magnification of the first pathological image.

(9)

The generation device according to any one of (1) to (8), wherein the generation unit generates the learning data on the basis of the second pathological image that is a pathological image obtained by imaging a section collected from the same specimen as a specimen of the first pathological image.

(10)

The generation device according to any one of (1) to (9), wherein the generation unit generates the learning data on the basis of the second pathological image that is a pathological image obtained by imaging the same slide as slide for the first pathological image.

(11)

The generation device according to any one of (1) to (10), wherein the generation unit generates the learning data to which a correction annotation is transcribed, the correction annotation being obtained by converting the annotation into an annotation corresponding to information regarding a second imaging device that has captured the second pathological image, and then further converting the converted annotation into an annotation corresponding to the second pathological image.

(12)

A generation device comprising:

an acquisition unit that acquires a first pathological image captured by a first imaging device, and an annotation that is information added to the first pathological image and is meta information related to the first pathological image; and a generation unit that generates learning data for evaluating pathological-related information based on a second pathological image according to the second pathological image captured by a second imaging device different from the first imaging device, the learning data being learning data obtained by transcribing the annotation in a manner corresponding to the second pathological image.

(13)

A generation method performed by a computer, comprising:

acquiring a first pathological image captured, and an annotation that is information added to the first pathological image and is meta information related to the first pathological image; and generating learning data for evaluating pathological-related information based on a second pathological image according to the second pathological image different from the first pathological image, the learning data being learning data obtained by transcribing the annotation in a manner corresponding to the second pathological image.

(14)

A generation method performed by a computer, comprising:

acquiring a first pathological image captured by a first imaging device, and an annotation that is information added to the first pathological image and is meta information related to the first pathological image; and generating learning data for evaluating pathological-related information based on a second pathological image according to the second pathological image captured by a second imaging device different from the first imaging device, the learning data being learning data obtained by transcribing the annotation in a manner corresponding to the second pathological image.

REFERENCE SIGNS LIST

1 INFORMATION PROCESSING SYSTEM
10 FIRST IMAGING DEVICE
20 SECOND IMAGING DEVICE
100 GENERATION DEVICE
110 COMMUNICATION UNIT
120 STORAGE UNIT
121 SLIDE STORAGE UNIT
122 SLIDE DATA STORAGE UNIT
123 ANNOTATION STORAGE UNIT
124 NEW SLIDE STORAGE UNIT
125 NEW SLIDE DATA STORAGE UNIT
126 TRANSCRIPTION ANNOTATION STORAGE UNIT
127 CORRECTION ANNOTATION STORAGE UNIT
128 MODEL STORAGE UNIT
129 COORDINATE CONVERSION INFORMATION STORAGE UNIT
130 CONTROL UNIT
131 ACQUISITION UNIT
132 CONVERSION UNIT
133 ADSORPTION UNIT
134 GENERATION UNIT
135 PROVISION UNIT
136 RETRIEVAL UNIT
N NETWORK

The invention claimed is:

1. A generation device, comprising:
   an acquisition unit configured to acquire a first pathological image, and an annotation that is information added to the first pathological image,
      wherein the annotation is meta information related to the first pathological image; and
   a generation unit configured to:
      convert the annotation into a transcription annotation that corresponds to a second pathological image; and
      generate, based on the transcription annotation, learning data to evaluate pathological-related information for the second pathological image, wherein
         the second pathological image is different from the first pathological image, and
         the learning data is the transcription annotation that is transcribed to the second pathological image.

2. The generation device according to claim 1, wherein the generation unit is further configured to generate the learning data based on of the second pathological image that is a pathological image that has a resolution different from a resolution of the first pathological image.

3. The generation device according to claim 2, wherein the generation unit is further configured to generate the learning data based on the second pathological image that is a pathological image that has visibility higher than visibility of the first pathological image.

4. The generation device according to claim 2, wherein the generation unit is further configured to generate the learning data based on the second pathological image that is a pathological image that has a resolution lower than resolution of the first pathological image.

5. The generation device according to claim 1, wherein the generation unit is further configured to generate the learning data based on the second pathological image that is a pathological image captured under a imaging condition different from an imaging condition of the first pathological image.

6. The generation device according to claim 5, wherein the generation unit is further configured to generate the learning data based on the second pathological image that is a pathological image captured by a imaging device different from an imaging device that has captured the first pathological image.

7. The generation device according to claim 5, wherein the generation unit is further configured to generate the learning data based on the second pathological image that is a pathological image captured at a magnification different from a magnification of the first pathological image.

8. The generation device according to claim 1, wherein
   the generation unit is further configured to generate the learning data based on the second pathological image, and
   the second pathological image is obtained based on an image of a section collected from a same specimen as a specimen of the first pathological image.

9. The generation device according to claim 8, wherein the generation unit is further configured to generate the learning data based on the second pathological image, and
   the second pathological image is obtained based on an image of a same slide as slide for the first pathological image.

10. The generation device according to claim 1, wherein the generation unit is further configured to generate the learning data to which a correction annotation is transcribed, and
    the correction annotation is obtained based on:
       conversion of the annotation into the transcription annotation that corresponds to information associated with a second imaging device that has captured the second pathological image, and
       conversion of the transcription annotation into the correction annotation that corresponds to the second pathological image.

11. A generation device, comprising:
    an acquisition unit configured to acquire a first pathological image captured by a first imaging device, and an annotation that is information added to the first pathological image,
       wherein the annotation is meta information related to the first pathological image; and
    a generation unit configured to:
       convert the annotation into a transcription annotation that corresponds to a second pathological image; and
       generate, based on the transcription annotation, learning data to evaluate pathological-related information for the second pathological image, wherein
          the second pathological image is captured by a second imaging device different from the first imaging device, and
          the learning data is the transcription annotation that is transcribed to the second pathological image.

12. A generation method, comprising:
    acquiring a first pathological image, and an annotation that is information added to the first pathological image, wherein the annotation is meta information related to the first pathological image;
    convert the annotation into a transcription annotation that corresponds to a second pathological image; and
    generating, based on the transcription annotation, learning data for evaluating pathological-related information the second pathological image, wherein
       the second pathological image is different from the first pathological image, and
       the learning data is the transcription annotation that is transcribed to the second pathological image.

13. A generation method, comprising:
    acquiring a first pathological image captured by a first imaging device, and an annotation that is information added to the first pathological image, wherein the annotation is meta information related to the first pathological image;
    converting the annotation into a transcription annotation that corresponds to a second pathological image; and
    generating, based on the transcription annotation, learning data for evaluating pathological-related information the second pathological image, wherein
       the second pathological image is captured by a second imaging device that is different from the first imaging device, and
       the learning data is the transcription annotation that is transcribed to the second pathological image.

* * * * *